US010039515B2

(12) United States Patent
Porter et al.

(10) Patent No.: US 10,039,515 B2
(45) Date of Patent: *Aug. 7, 2018

(54) METHODS FOR TREATING IDIOPATHIC PULMONARY FIBROSIS

(71) Applicant: FibroGen, Inc., San Francisco, CA (US)

(72) Inventors: Seth Porter, San Carlos, CA (US); John L Stauffer, Cupertino, CA (US)

(73) Assignee: FIBROGEN, INC., San Francisco, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/263,767

(22) Filed: Sep. 13, 2016

(65) Prior Publication Data
US 2017/0027535 A1   Feb. 2, 2017

Related U.S. Application Data

(63) Continuation of application No. 14/398,380, filed as application No. PCT/US2013/031599 on Mar. 14, 2013, now Pat. No. 9,480,449.

(60) Provisional application No. 61/642,366, filed on May 3, 2012.

(51) Int. Cl.
A61K 39/395    (2006.01)
A61B 6/00      (2006.01)
A61B 6/03      (2006.01)
C07K 16/22     (2006.01)
A61K 39/00     (2006.01)
A61K 49/00     (2006.01)

(52) U.S. Cl.
CPC ............ A61B 6/5217 (2013.01); A61B 6/032 (2013.01); A61B 6/50 (2013.01); A61K 49/0004 (2013.01); C07K 16/22 (2013.01); A61K 2039/505 (2013.01)

(58) Field of Classification Search
None
See application file for complete search history.

(56) References Cited

U.S. PATENT DOCUMENTS

| 5,770,209 | A | 6/1998 | Grotendorst et al. |
| 6,492,129 | B1 | 12/2002 | Grotendorst |
| 7,115,390 | B1 | 10/2006 | Grotendorst et al. |
| 7,718,177 | B2 | 5/2010 | Grotendorst |
| 2003/0113816 | A1 | 6/2003 | Weitz et al. |
| 2004/0248206 | A1 | 12/2004 | Lin et al. |
| 2007/0160580 | A1 | 7/2007 | Bradford |
| 2010/0022568 | A1 | 1/2010 | Clozel et al. |
| 2015/0210760 | A1* | 7/2015 | Modelska ............... C07K 16/22 424/130.1 |

FOREIGN PATENT DOCUMENTS

| EP | 1043335 | 10/2000 |
| WO | WO 2009/026428 | 2/2009 |
| WO | WO 2011/056234 | 5/2011 |
| WO | WO 2012/061811 | 5/2012 |

OTHER PUBLICATIONS

Ahmed, M.S., et al., "Induction of Pulmonary Connective Tissue Growth Factor in Heart Failure is Associated With Pulmonary Parenchymal and Vascular Remodeling," Cardio. Res. (2007) 74:323-333.
Bhatt, N., et al., "Promising Pharmacologic Innovations in Treating Pulmonary Fibrosis," Current Opin in Pharm. (2006) 6:284-292.
Guha, M., "Specific Down-Regulation of Connective Tissue Growth Factor Attenuates Progression of Nephropathy in Mouse Models of Type 1 and Type 2 Diabetes," FASEB Jour. (2007) 21:1-14.
Kothapalli, D., "Transforming Growth Factor B Induces Anchorage-Independent Growth of NRK Fibroblasts via a Connective Tissue Growth Factor-Dependent Signaling Pathway," Cell Growth & Differ. (1997) vol. 8, 61-68.
Lai, T.-C., et al., "Small Interfering RNAs (siRNAs) Targeting TGF-B1 mRNA Suppress Asbestos-Induced Expression of TGF-B1 and CTGF in Fibroblasts," J. Environ. Path. (2009) 28(2):109-119.
Li, C., et al., "Role of Connective Tissue Growth Factor (IGFBP-8) in Radiation-Induced Lung Fibrosis (RILF)," Inter. Jour. Rad. Oncol. (2008) vol. 72, No. 1 (Abstract).
Ostrau, C., et al., "Lovastatin Attenuates Ionizing Radiation-induced Normal Tissue Damage In Vivo," Radio. & Oncol. (2009) 92:492-499.
Ponticos, M., et al., "Pivotal Role of Connective Tissue Growth Factor in Lung Fibrosis," Arthritis & Rheumat. (2009) vol. 60, (7):2142-2155.
Shimo, T., "Inhibition of Endogenous Expression of Connective Tissue Growth Factor by Its Antisense Oligonucleotide and Antisense RNA Suppresses Proliferation and Migration of Vascular Endothelial Cells," J. Biochem. (1998) 124, 130-140.
Bickelhaupt, S., et al., "Attenuation and Reversal of Radiation-Induced Pulmonary Fibrosis in a Murine Model by an Anti-CTGF Monoclonal Antibody," Int. J. Radiat. Oncol. (2010) 78:Suppl. (Abstract).
Thannickal, V., et al., "Idiopathic Pulmonary Fibrosis: Emerging Concepts on Pharmacotherapy," Expert Opin, Pharmacosher. (2004) 5(8):1671-1686.
Uchio, K., et al., "Down-Regulation of Connective Tissue Growth Factor and Type I Collagen mRNA Expression by Connective Tissue Growth Factor Antisense Oligonucleotide During Experimental Liver Fibrosis," Wound Repair Regen. (2004)60-66.
Williams, J.A., et al., "Effect of Administration of Lovastatin on the Development of Late Pulmonary Effects after Whole-Lung Irradiation in a Murine Model," Rad. Res. (2004) 161:560-567.
Anonymous, FibroGen Announces Preliminary Data From an Open-Label Phase 2 Study to Evaluate the Safety and Efficacy of FG-3019 in Individuals With Idiopathic Pulmonary Fibrosis (IPF) and Provides Program Update, http://investor.fibrogen.com/phoenix.zhtml?c=253783&p=irol-newsArticle&ID=1983434.

(Continued)

Primary Examiner — Marianne P Allen

(57) ABSTRACT

The present invention relates to methods and medicaments useful for treating idiopathic pulmonary fibrosis (IPF) by administering anti-CTGF antibodies. Methods for prognosing individuals with IPF are also provided.

5 Claims, 17 Drawing Sheets

(56) References Cited

OTHER PUBLICATIONS

Anonymous, Safety, Tolerability, and Efficacy Study of Idiopathic Pulmonary Fibrosis (FGCL-3019-049) https://clinicaltrials.gov/show/NCT01262001.

Anonymous, View of NCT01262001 on Dec. 16, 2010. https://clinicaltrials.gov/archive/NCT01262001/2010_12_16.

Anonymous, View of NCT01262001 on Jul. 8, 2011, https://clinicaltrials.gov/archive/NCT01262001/2011_07_08.

Anonymous, View of NCT01262001 on May 15, 2012, https://clinicaltrials.gov/archive/NCT01262001/2012_05_15.

Magento Y et al., Safety and Tolerablitiy of Human Monoclonal Antibody FG-3019, Anti-Connective Tissue Growth Factor, in Patients with Idiopathic Pulmonary Fibrosis, http://journal.publications.chestnet.org/article.aspx?articleid=1091696.

Thannickal VJ et al., Emerging drugs for idiopathic pulmonary fibrosis, Expert Opin Emerg Drugs. Nov. 2005:10 (4):707-27.

Raghu et al., Am J Respir Crit Care Med vol. 183, pp. 788-824, 2011.

* cited by examiner

METHODS FOR TREATING IDIOPATHIC PULMONARY FIBROSIS

CROSS REFERENCE TO RELATED APPLICATIONS

This application is a continuation of U.S. application Ser. No. 14/398,380, filed 31 Oct. 2014, now U.S. Pat. No. 9,480,449, which is a U.S. National Stage Application under 35 U.S.C. § 371 from International Application No. PCT/US2013/031599 filed 14 Mar. 2013, that claims the benefit under 35 U.S.C. § 119(e) of U.S. Provisional Application 61/642366 filed. May 3, 2012.

FIELD OF THE INVENTION

The present invention relates to methods and medicaments useful for treating idiopathic pulmonary fibrosis. Methods for prognosing individuals with IPF are also provided.

BACKGROUND OF THE INVENTION

IPF is a chronic and progressive lung disease that results in respiratory failure and death. Median survival is about 2 to 4 years from diagnosis. The etiology of IPF remains unknown, but the disease is characterized by fibrotic interstitial infiltrates that are consistent with the histopathologic pattern of usual interstitial pneumonia. (Gross T J et al. *N Engl J Med* (2001); 345:(7):517-525.) As interstitial fibrosis advances with accompanying distortion of lung architecture, the lung becomes less compliant, increasing the effort associated with breathing, leading to dyspnea. Typically, lung function declines slowly over time, but some patients experience rapid declines that can lead to hospitalization or death, particularly in later stages of the disease. (Martinez F J et al. *Ann Intern Med* (2005) 142:963-967.)

In the United States, as many as 89,000 people are afflicted with IPF, with about 34,000 newly diagnosed annually. (Raghu G et al., *Am J Respir Crit Care Med* (2006) 174: (7):810-816.) Prevalence of IPF ranges from 14.0 to 42.7 cases per 100,000 persons and the annual incidence ranges from 6.8 to 16.3 cases per 100,000 persons, depending on the strictness of the diagnostic criteria employed. (Raghu G et al., supra.) The prevalence of IPF increases with age, with most IPF patients 60 years of age or older at the time of diagnosis. The disease is more common in men than in women (Fernandez Perez E R et al. *Chest* (2010) 137: (1):129-137,) with most patients current or former smokers. A familial form of IPF may account for as many as 20% of IPF cases. (Loyd J E, *Eur Respir Rev* (2008) 17:(109):163-167.)

While the pathogenesis of IPF is not clearly defined, the disease is believed to be caused by repetitive epithelial injury. (Selman M et al. *Ann Intern Med* (2001) 134:136-151; Selman M. *Proc Am Thorac Soc* (2006) (4):364-372.) According to this hypothesis, alveolar cell injury and activation initiate a dysregulated, exaggerated fibrotic healing process characterized by myofibroblast proliferation and progressive deposition of extracellular matrix (ECM) in genetically susceptible individuals. (Selman M et al. (2001) supra; Selman M. (2006) supra.)

There are currently no FDA-approved drugs for the treatment of IPF. Recently conducted phase 3 clinical trials of pirfenidone, sildenafil, bosentan, etanercept, and interferon gamma-1b have failed to demonstrate efficacy in their primary endpoints. N-acetyl cysteine (NAC), corticosteroids, and the immunosuppressive drugs cyclophosphamide and azathioprine are commonly prescribed, but there is little evidence that use of these drugs improves patient outcome or alters the natural course of the disease. (Collard H R et al. *Chest* (2004) 125: (6):2169-2174, Walter N et al, *Proc Am Thorac Soc* (2006) 3: (4):377-381.) In fact, the combination of prednisone, azathioprine, and NAC produced a worse outcome than NAC or placebo in a recent IPF study. (NIH News, Oct. 24, 2011.) Lung transplantation is the only treatment that improves survival (Walter, supra.), but most IPF patients are not eligible for transplantation because of their age or comorbid conditions. IPF patients usually are managed with supportive measures such as symptomatic treatment of cough and dyspnea, supplemental oxygen for hypoxemia, smoking cessation, pulmonary rehabilitation, and prophylaxis and control of respiratory tract infections.

The progressive and fatal course of IPF coupled with the absence of approved drugs underscore the need for new methods and agents to treat this devastating disease. The present invention meets this unmet medical need by providing novel methods and agents for use in treating IPF. In particular, the present invention provides agents and methods for reducing, stabilizing or reversing the progression and severity of IPF and for preventing or treating one or more symptoms of IPF by inhibiting connective tissue growth factor (CTGF) activity.

SUMMARY OF THE INVENTION

In one aspect of the invention, a method is provided for treating IPF in a subject in need thereof, wherein the method comprises administering to the subject an effective amount of an anti-CTGF antibody, thereby treating IPF. In some embodiments, the method for treating IPF with an anti-CTGF antibody reducing the pathologic rate of decline of a pulmonary function parameter by at least 5%. In further embodiments, the pulmonary function parameter is selected from the group consisting of vital capacity (VC), residual volume (RV), forced expiratory volume (FEV), forced vital capacity (FVC), forced vital capacity percent (FVC %) predicted, forced expiratory flow (FEF), peak expiratory flow rate (PEFR), inspiratory reserve volume (IRV), functional residual capacity (FRC), inspiratory capacity (IC), total lung capacity (TLC), expiratory reserve volume (ERV), tidal volume (TV), and maximum voluntary ventilation (MVV).

The additional embodiments, the method for treating IPF with an anti-CTGF antibody comprises increasing the subject's FVC by at least 0.05 liters compared to a baseline FVC measurement. In further embodiments, the method for treating IPF comprises increasing the subject's FVC % predicted by at least 0.5% compared to a baseline FVC % predicted measurement.

In other embodiments, the method for treating IPF with an anti-CTGF antibody comprises producing at least a 5% increase, compared to a baseline measurement, in diffusing capacity of the lung for carbon monoxide (DLCO) corrected for hemoglobin, DLCO percent (DLCO %) predicted, or arterial oxyhaemoglobin saturation ($SaO_2$). In further embodiments, the method for treating IPF produces a decrease of at least 5% in alveolar-arterial oxygen tension gradient (A-a) $PO_2$.

In additional embodiments, the method for treating IPF with an anti-CTGF antibody comprises at least a 5% reduction, compared to a baseline measurement, in the extent of pulmonary infiltration of fibroblasts or myofibroblasts, at least a 5% reduction in the rate of collagen deposition, at least a 5% reduction in the degree type II pneumocyte hyperplasia, at least a 5% reduction in the degree of smooth muscle hyperplasia or at least a 5% reduction in the formation of fibroblastic foci.

In other embodiments, the method for treating IPF comprises stabilizing or producing at least a 2% reduction, compared to a baseline measurement, in one or more pulmonary radiographic parameters selected from the group consisting of ground glass opacities, fibrosis, and honeycomb formation.

In further embodiments, the method for treating IPF comprises extending the subject's progression-free survival or overall survival of at least 1 month compared to historic controls. In other embodiments, the treatment method comprises decreasing the subject's risk of death at 1 year post-diagnosis by at least 10% compared to historical controls.

In still other embodiments, the method for treating IPF comprises preventing a worsening of dyspnea or the development of new dyspnea, reducing the frequency or intensity of coughing, preventing a worsening of hypoxemia; reducing the number or severity of acute exacerbations of IPF, reducing the number of IPF-related hospital admissions, reducing the need for supplemental oxygen, or improving the assessment of health-related quality of life.

In some embodiments, the method for treating IPF comprises the use of an anti-CTGF antibody that has the same amino acid sequence as the antibody produced by the cell line identified by ATCC Accession No. PTA-6006. In other embodiments, the anti-CTGF antibody used in the treatment method binds to CTGF competitively with an antibody produced by the cell line identified by ATCC Accession No. PTA-6006.

In further embodiments, the method for treating IPF comprises administering at least 15 mg/kg of an anti-CTGF antibody. In other embodiments, at least 1.00 g of an anti-CTGF antibody is administered. In additional embodiments, the treatment method is associated with a $C_{min}$ of at least 10.0 μg/ml for the anti-CTGF antibody when measured at 21 days post-administration. In other embodiments, the treatment method produces an area under the curve for the anti-CTGF antibody for the period of 0-21 days post-administration of at least 1,000 μg*h/ml.

In some embodiments, the method for treating IPF further comprises administering an additional therapeutic agent selected from the group consisting of corticosteroids, antibiotics, immunosuppressive drugs, supplemental oxygen, and mechanical ventilation.

In some embodiments, the subject to be treated with the treatment method has a forced vital capacity percent (FVC %) predicted of greater than about 55%, less than 50% parenchymal fibrosis, less than 25% honeycombing within the whole lung or has been diagnosed with IPF for less than 5 years.

In one aspect, the invention provides a pharmaceutical composition comprising an anti-CTGF antibody for treating IPF.

These and other embodiments of the present invention will readily occur to those of skill in the art in light of the disclosure herein, and all such embodiments are specifically contemplated.

Each of the limitations of the invention can encompass various embodiments of the invention. It is, therefore, anticipated that each of the limitations of the invention involving any one element or combinations of elements can be included in each aspect of the invention. This invention is not limited in its application to the details of construction and the arrangement of components set forth in the following description or illustrated in the drawings. The invention is capable of other embodiments and of being practiced or of being carried out in various ways. Also, the phraseology and terminology used herein is for the purpose of description and should not be regarded as limiting. The use of "including," "comprising," or "having," "containing," "involving," and variations thereof herein, is meant to encompass the items listed thereafter and equivalents thereof as well as additional items.

DESCRIPTION OF THE INVENTION

Figure 1:
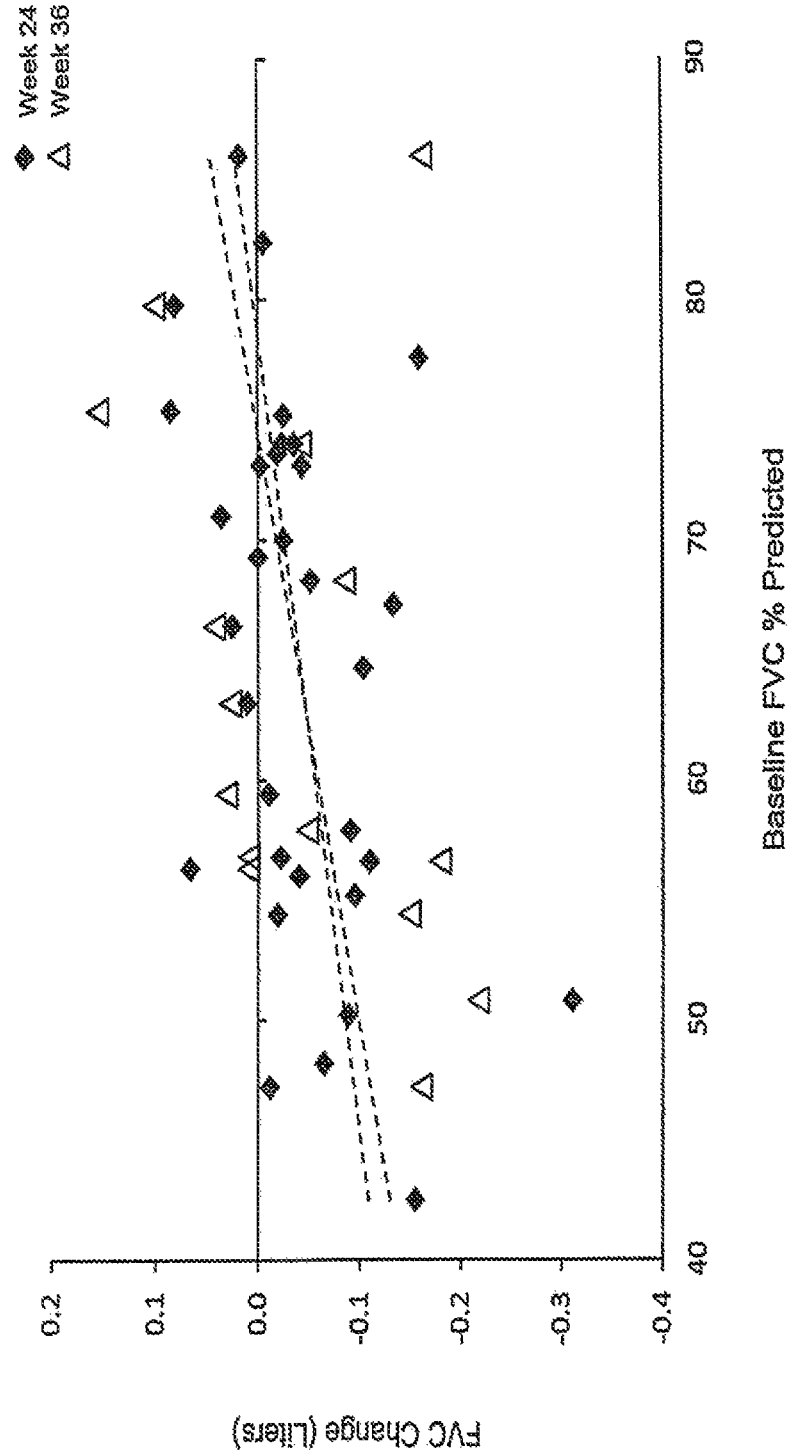
FIG. 1 illustrates the change from baseline in forced vital capacity (FVC) in liters at Weeks 24 and 36 following initiation of anti-CTGF antibody treatment versus the baseline FVC percent (FVC %) predicted of subjects with moderate to severe IPF. The change in FVC over time correlates with baseline FVC % predicted values. Subjects above about a baseline FVC % predicted of 55% demonstrate, in general, stable or improved (positive change) FVC, while subjects below about a baseline FVC % predicted of 55% demonstrate, in general, a decline in FVC. Baseline FVC % predicted was calculated from the mean of a subject's FVC % predicted values from screening 1 visit and treatment Day 1. The median baseline FVC % predicted was 63.2%.

Unless defined otherwise, all technical and scientific terms used herein have the same meanings as commonly understood by one of ordinary skill in the art to which this invention belongs. Although any methods and materials similar or equivalent to those described herein can be used in the practice or testing of the present invention, the preferred methods, devices, and materials are now described. All publications cited herein are incorporated herein by reference in their entirety for the purpose of describing and disclosing the methodologies, reagents, and tools reported in the publications that might be used in connection with the present invention. Nothing herein is to be construed as an admission that the present invention is not entitled to antedate such disclosure by virtue of prior invention.

The practice of the present invention will employ, unless otherwise indicated, conventional methods of chemistry, biochemistry, molecular biology, cell biology, genetics, immunology and pharmacology, within the skill of the art. Such techniques are explained fully in the literature. See, e.g., Gennaro, A. R., ed. (1990) *Remington's Pharmaceutical Sciences*, 18th ed., Mack Publishing Co.; Colowick, S. et al., eds., *Methods In Enzymology*, Academic Press, Inc.; *Handbook of Experimental Immunology*, Vols. I-IV (D. M. Weir and C. C. Blackwell, eds., 1986, Blackwell Scientific Publications); Maniatis, T. et al., eds. (1989) *Molecular Cloning: A Laboratory Manual*, 2nd edition, Vols. I-III, Cold Spring Harbor Laboratory Press; Ausubel, F. M. et al., eds. (1999) *Short Protocols in Molecular Biology*, 4th edition, John Wiley & Sons; Ream et al., eds. (1998) *Molecular Biology Techniques: An Intensive Laboratory Course*, Academic Press); *PCR (Introduction to Biotechniques Series)*, 2nd ed. (Newton & Graham eds., 1997, Springer Verlag).

Definitions

As used herein, the term "about" refers to ±10% of the numerical value of the number with which it is being used. Therefore, about 50% means in the range of 45%-55%.

As used herein and in the appended claims, the singular form "a," "an," and "the" include plural references unless the context clearly dictates otherwise. For example, a reference to "an anti-CTGF agent" includes a plurality of such agents; a reference to an "antibody" is a reference to one or more antibodies and to equivalents thereof known to those skilled in the art; and so forth.

As used herein, the term "subject," "host," "individual," and "patient" are used interchangeably to refer to a mammal. In a preferred embodiment, the mammal is a primate, and more preferably a human being.

As used herein, the term "blood" encompasses whole blood, serum or plasma. When a specific antibody concentration in plasma, e.g., a target antibody plasma level, is discussed, it is to be understood to include the antibody concentration in whole blood, serum or plasma.

The terms "idiopathic pulmonary fibrosis" and "IPF" describe a chronic, progressive fibrosing interstitial pneumonia of unknown cause, limited to the lungs and associated with the radiologic and/or histopathologic pattern of usual interstitial pneumonia (UIP).

Subjects with IPF have a UIP pattern on high resolution computerized tomography (HRCT) scan with the following three features: (1) subpleural, basal predominance of fibrosis; (2) reticular abnormality; and (3) presence of honeycombing with or without traction bronchiectasis. Additionally, IPF subjects do not have any of the following features inconsistent with an UIP pattern: (i) upper or mid-lung predominance of fibrosis; (ii) peribronchovascular predominance fibrosis; (iii) extensive ground glass abnormality (extent>reticular abnormality); (iv) profuse micronodules (bilateral, predominately upper lobes); (v) discrete cysts (multiple, bilateral away from areas of honeycombing); (vi) diffuse mosaic attenuation/air trapping (bilateral, in three or more lobes); and (vii) consolidation in bronchopulmonary segment(s) and/or lobe(s). These criteria represent the official statement of the American Thoracic Society (ATS), The European Respiratory Society (ERS), The Japanese Respiratory Society (JRS), And The Latin American Thoracic Association (ALAT). (See Raghu G, et al. *Am J Respir Crit Care Med.* (2011) 183: (6):788-824.)

Subjects with IPF can also have a possible UIP pattern on HRCT scan with histopathological confirmation of UIP. The subjects have the following two features present on their HRCT scan: (1) subpleural, basal predominance of fibrosis; and (2) reticular abnormality. Additionally, the following features that are inconsistent with a UIP pattern are absent: (i) upper or mid-lung predominance of fibrosis; (ii) peribronchovascular predominance of fibrosis; (iii) extensive ground glass abnormality (extent>reticular abnormality); (iv) profuse micronodules (bilateral, predominately upper lobes); (v) discrete cysts (multiple, bilateral away from areas of honeycombing); (vi) diffuse mosaic attenuation/air trapping (bilateral, in three or more lobes); and (vii) consolidation in bronchopulmonary segment(s) and/or lobe(s). (See Raghu G, et al. supra)

For histopathological confirmation of UIP pattern, the following four criteria are met: (1) evidence of marked fibrosis/architectural distortion, ±honeycombing in a predominantly subpleural/paraseptal distribution; (2) presence of patchy involvement of lung parenchyma by fibrosis; (3) presence of fibroblast foci; and (4) absence of features against a diagnosis of UIP suggesting an alternate diagnosis, e.g., hyaline membranes, organizing pneumonia, granulomas, marked interstitial inflammatory cell infiltrate away from honeycombing, predominant airway centered changes, etc. (See Raghu, supra)

As used herein, the terms "treating", "treatment," and "therapy," in the context of the invention, mean the administration of an anti-CTGF antibody to subjects with IPF or at risk for developing IPF. In some embodiments, the subjects with IPF are "unresponsive to conventional treatment," i.e., unresponsive to conventional prior art treatments of IPF including corticosteroids, cyclophosphamide, and azathioprine. In further embodiments, the IPF subjects treated with anti-CTGF antibodies have responded to conventional treatment and the anti-CTGF antibodies are being administered after the cessation of conventional treatments or in addition to conventional treatments. In other embodiments, the IPF subjects treated with anti-CTGF antibody are those subjects that are treatment naïve and include newly diagnosed IPF subjects.

As used herein, the terms "effective amount" or "therapeutically effective amount" in the context of administering an anti-CTGF antibody to a subject, refer to the amount of an anti-CTGF antibody that is sufficient to produce a beneficial or therapeutic effect including a partial or complete cure of IPF, or the alleviation, amelioration, stabilization, improvement, or reversal of the disease or any associated symptoms of the disease. In some embodiments, an associated symptom of IPF is the pathologic rate of decline in one or more pulmonary function parameters, discussed below. In specific embodiments, an "effective amount" of an anti-CTGF antibody refers to an amount of an anti-CTGF antibody that is sufficient to produce at least one or more of the following effects compared to baseline, i.e., pretreatment: (i) a reduction in a pathologic rate of decline for one or more pulmonary function parameters; (ii) a stabilization (arrest or stasis) in the pathologic rate of decline in one or more pulmonary function parameters; or (iii) a reversal in pathologic rate of decline in one or more pulmonary function parameters, including the normalization of one or more pulmonary function parameters.

Lung capacity and associated pulmonary function parameters naturally decline due to aging. Numerous normal populations have been studied and the rate of decline of lung capacity and various pulmonary function parameters have been calculated and are readily available in the art. (Crapo et al. (1981) *Am. Rev. Respir. Dis.* 123:659-664.) For example, a 65 year-old Caucasian male who is 183 cm (6'0") tall has a predicted FVC of 4.95 liters. At age 66 this same male has a predicted FVC of 4.92 liters. This difference of 0.03 liters represents the expected decline due to aging by 1 year. Similarly, a 62 year-old Caucasian woman who is 167 cm (about 5'6") has a predicted FVC of 2.67 liters. At age 63, this same female has a predicted FVC of 2.64 liters. This difference of 0.03 liters represents the expected decline due to aging by 1 year.

In contrast to the natural decline due to aging, subjects with IPF have an abnormally steep rate of decline in lung capacity or in one or more pulmonary function parameters, i.e., a "pathologic rate of decline." As used herein, a "pathologic rate of decline" is a rate of decline in lung capacity or in one or more pulmonary function parameters that is at least 5% greater than the decline due to normal aging. In some embodiments, a pathologic rate of decline is at least 5%, 10%, 15%, 20%, 25%, 30%, 40%, 50%, 60%, 70%, 80%, 90%, 100%, 125%, 150%, 200%, 300%, 400%, 500%, 600%, 700%, 800% or 1000% greater than the predicted rate of decline for a normal person of similarly matched race or ethnicity, gender, age, height, and weight. Rates of decline can be expressed as the change from baseline per 1 week, 2 weeks, 4 weeks, 8 weeks, 12 weeks, 24 weeks, 36 weeks, 48 weeks, or 12 months. In particular embodiments, the pathologic rate of decline in lung capacity is the change in forced vital capacity (FVC) from baseline of at least about −0.05 liters, −0.10 liters, −0.15 liters, −0.20 liters or −0.25 liters per 12 months. In other embodiments, the pathological rate of decline is the change from baseline forced vital capacity percent (FVC %) predicted of at least about −2%, −3%, −4%, −5%, −6%, −7%, −8% or −10% per 12 months.

In some embodiments, a method is provided for increasing FVC % predicted in a subject with IPF by administering an effective amount of an anti-CTGF antibody. In further embodiments, treatment with an effective amount of an anti-CTGF antibody increases FVC % predicted by at least 0.5%, 1%, 1.5%, 2.0%, 2.5%, 3.0%, 4.0%, 5.0%, 6.0%, 7.0%, 8.0%, 9.0%, 10%, 15%, 20%, 30%, 40% or 50% compared to baseline FVC % predicted. In further embodiments, treatment with the anti-CTGF antibody is for at least 3 weeks, 6 weeks, 9 weeks, 12 weeks, 15 weeks, 18 weeks, 21 weeks, 24 weeks, 27 weeks, 30 weeks, 33 weeks, 36 weeks or 48 weeks. In other embodiments, treatment is for 3 weeks or less, 6 weeks or less, 9 weeks or less, 12 weeks or less, 18 weeks or less, 24 weeks or less, 36 weeks or less, 48 weeks or less, 12 months or less, 16 months or less, 20 months or less, or 24 months or less from starting treatment with an anti-CTGF antibody. For example, if a subject with IPF has a baseline FVC % predicted of 65%, treatment with an anti-CTGF antibody raises the subject's FVC % predicted to 66.5% at week 36 post-initiation of therapy.

Numerous pulmonary function parameters known in the art can be used to determine an effective amount of an anti-CTGF antibody, i.e., an amount to reduce, stabilize or reverse a pathologic rate of decline in one or more pulmonary function parameters; or to monitor patient response to anti-CTGF antibody therapy. These pulmonary function parameters include the following:

Vital capacity (VC) is the total volume of air that can be moved in and out of the lungs. VC is equal to the combined inspiratory reserve volume, tidal volume, and expiratory reserve volume.

Forced vital capacity (FVC) is the vital capacity from a maximally forced expiratory effort.

FVC % predicted is a subject's measured FVC expressed as the percentage of the predicted FVC for the subject. As used herein, all FVC % predicted values are absolute values and not relative values.

Residual volume (RV) is the volume of air remaining in the lungs after a maximal exhalation.

Forced expiratory volume (FEV) is the expiratory volume of air from a maximally forced expiratory effort, usually measured over a set period of time, e.g., 1 second, FEV1; 6 seconds, FEV6; etc.

Forced inspiratory flow (FIF) is the inspiratory volume of air from a maximally forced inspiratory effort, usually measured over a set period of time, e.g., 1 second, FIF1; 6 seconds, FIF6; etc.

Peak expiratory flow rate (PEFR) is the highest forced expiratory flow rate.

Inspiratory reserve volume (IRV) is the maximal volume that can be inhaled after a normal inspiration, measured from the end-inspiratory level.

Tidal volume (TV) is the volume of air inhaled or exhaled during one respiratory cycle, typically measured at rest.

Inspiratory capacity (IC) is the sum of the inspiratory reserve volume and the tidal volume.

Functional residual capacity (FRC) is the sum of the expiratory reserve volume and the residual volume. Typically, FRC represents the volume of air in the lungs at the end of a normal expiration.

Total lung capacity (TLC) is the sum of the vital capacity and residual volume that represents the total volume of air that can be contained in the lung.

Expiratory reserve volume (ERV) is the maximal volume of air that can be exhaled after a normal expiration, measured from the end-expiratory position.

Maximum voluntary ventilation (MVV) is the volume of air expired in a specified time period during repetitive maximal effort.

FEV1/FVC ratio means the ratio between forced expiratory volume in one second and forced vital capacity.

Many of these pulmonary function parameters are readily obtainable through the use of a spirometer as is well-known in the art. Residual volume can be obtained through indirect methods such as radiographic planimetry, body plethysmography, closed circuit dilution (including the helium dilution technique), and nitrogen washout.

In some embodiments, a method is provided for reducing, stabilizing, or reversing a pathologic rate of decline in one or more pulmonary function parameters, comprising the administration of an effective amount of an anti-CTGF antibody. In further embodiments, treatment with an effective amount of an anti-CTGF antibody reduces the pathologic rate of decline of one or more pulmonary function parameters by at least 5%, 10%, 15%, 20%, 30%, 40%, 50%, 60%, 80%, or 100%. In particular embodiments, the pulmonary function parameter is FVC % predicted. In further embodiments, the reduction, stabilization or reversal in the pathologic rate of decline is achieved in 3 weeks or less, 6 weeks or less, 9 weeks or less, 12 weeks or less, 18 weeks or less, 24 weeks or less, 36 weeks or less, 48 weeks or less, 12 months or less, 16 months or less, 20 months or less, or 24 months or less from starting treatment with an anti-CTGF antibody.

In some embodiments, a method is provided for increasing FVC of a subject with IPF by administering an effective amount of an anti-CTGF antibody. In further embodiments, treatment with an effective amount of an anti-CTGF antibody increases FVC by at least 0.05 liters, 0.1 liters, 0.15 liters, 0.20 liters, 0.25 liters or 0.3 liters compared to baseline FVC. In further embodiments, treatment with the anti-CTGF antibody is for at least 3 weeks, 6 weeks, 9 weeks, 12 weeks, 15 weeks, 18 weeks, 21 weeks, 24 weeks, 27 weeks, 30 weeks, 33 weeks, 36 weeks or 48 weeks. In other embodiments, treatment is for 3 weeks or less, 6 weeks or less, 9 weeks or less, 12 weeks or less, 18 weeks or less, 24 weeks or less, 36 weeks or less, 48 weeks or less, 12 months or less, 16 months or less, 20 months or less, or 24 months or less from starting treatment with an anti-CTGF antibody. For example, if a subject with IPF has a baseline FVC 2.61 liters, treatment with an anti-CTGF antibody raises the subject's FVC to 2.66 liters at week 48 post-initiation of therapy Additionally, an effective amount of an anti-CTGF antibody also refers to an amount of an anti-CTGF antibody that is sufficient to produce: (i) an increase in diffusing capacity of the lung for carbon monoxide (DLCO) corrected for hemoglobin compared to baseline, i.e., pretreatment: (ii) an increase in the DLCO percent (DLCO %) predicted compared to baseline; (iii) an increase in arterial oxyhaemoglobin saturation ($SaO_2$) compared to baseline; or (iv) a decrease in alveolar-arterial oxygen tension gradient (A-a) $PO_2$ compared to baseline. In some embodiments, the increase in DLCO, DLCO % predicted, or $SaO_2$ is at least 5%, 10%, 15%, 20%, 25%, 30%, 35%, 40%, 45%, 50%, 55%, 60%, 65%, 70%, 75%, 80%, or 90% above the baseline value. In other embodiments, the decrease in (A-a) $PO_2$ is at least 5%, 10%, 15%, 20%, 25%, 30%, 35%, 40%, 45%, 50%, 55%, 60%, 65%, 70%, 75%, 80%, or 90% below the baseline value, DLCO, DLCO % predicted, $SaO_2$, or (A-a) $PO_2$ can be measured at rest or after exercise, e.g., the standardized 6-minute walk test.

In further embodiments, an effective amount of an anti-CTGF antibody can induce a desired change in DLCO, DLCO % predicted, $SaO_2$, or (A-a) $PO_2$ value in 3 weeks or less, 6 weeks or less, 9 weeks or less, 12 weeks or less, 18 weeks or less, 24 weeks or less, 36 weeks or less, 48 weeks or less, 12 months or less, 16 months or less, 20 months or less, or 24 months or less from starting treatment with an anti-CTGF antibody.

Further, an effective amount of an anti-CTGF antibody additionally refers to the amount of an anti-CTGF antibody that is sufficient to produce a reduction, stabilization, or reversal of at least one or more of the following histopathologic features compared to baseline: (i) degree of pulmonary infiltration of fibroblasts and/or myofibroblasts; (ii) rate of collagen deposition; (iii) degree of type II pneumocyte hyperplasia; (iv) degree of smooth muscle hyperplasia, or (v) formation of fibroblastic foci (buds of young proliferating fibroblasts adjacent to alveoli). Typically, these histopathological features are more commonly seen in subpleural regions of the lower lung zones. In some embodiments, an effective amount of an anti-CTGF antibody is sufficient to produce a reduction of at least 1%, 2%, 3%, 4%, 5%, 10%, 15%, 20%, 25%, 30%, 35%, 40%, 45%, 50%, 55%, 60%, 65%, 70%, 75%, 80%, 85%, 90%, or 95% in at least one or more histopathologic feature compared to baseline. In further embodiments, the reduction in one or more histopathological feature is achieved in 3 weeks or less, 6 weeks or less, 9 weeks or less, 12 weeks or less, 18 weeks or less, 24 weeks or less, 36 weeks or less, 48 weeks or less, 12 months or less, 16 months or less, 20 months or less, or 24 months or less from starting treatment with an anti-CTGF antibody.

Additionally, an effective amount of an anti-CTGF antibody additionally refers to the amount of an anti-CTGF antibody that is sufficient to produce a reduction, stabilization, or reversal of at least one or more of the following pulmonary radiographic parameters compared to baseline: (i) degree of ground glass opacities; (ii) degree of fibrosis; and (iii) degree of honeycomb appearance of pulmonary architecture. Typically, these pulmonary radiographic parameters are evaluated by HRCT scans. For example, see Kim et al. *Clin Exp Rheumatol.* (2010) 28(5 Suppl 62):S26-S35; Kim et al. *Eur Radiol* (2011) 21: 2455-2465. As used herein, "stabilization" means the pulmonary radiographic parameter is substantially unchanged from baseline, i.e., within the error of measurement for the particular technique. As used herein, a "reduction" in a pulmonary radiographic parameter means a lessening of the severity of the parameter. Reductions of <-2% in a pulmonary radiographic parameter compared to baseline for whole lung, are categorized as "reversals." For example, if CAD analysis of a HRCT scan from Week 24 shows that the pulmonary radiographic parameter fibrosis is -5% compared to the baseline value, then the response is categorized as a reversal of the extent of lung fibrosis. Reductions in pulmonary radiographic parameters can also be measured serially, e.g., a comparison of HRCT scans at Weeks 24 and 48 compared to baseline may show an initial stabilization at Week 24 that continues to a reversal of the pulmonary radiographic parameter at Week 48.

In some embodiments, an effective amount of an anti-CTGF antibody is sufficient to produce a reduction, stabilization, or reversal in at least one or more pulmonary radiographic parameters compared to baseline. In other embodiments, an effective amount of an anti-CTGF antibody is sufficient to reduce at least one pulmonary radiographic parameter compared to baseline by at least 1%, 2%, 3%, 4%, 5%, 6%, 7%, 8%, 9%, 10%, 15%, 20%, 25%, 30%, 35%, 40%, 45% or 50%. For example, treatment with an effective amount of an anti-CTGF antibody reduces the pulmonary radiographic parameter ground glass opacities, fibrosis or honey comb appearance or QILD by at least 2% for whole lung compared to a baseline measurement resulting in a reversal of the pulmonary radiographic parameter. In further embodiments, the reduction, stabilization, or reversal in one or more pulmonary radiographic parameters is achieved in 3 weeks or less, 6 weeks or less, 9 weeks or less, 12 weeks or less, 18 weeks or less, 24 weeks or less, 36 weeks or less, 48 weeks or less, 12 months or less, 16 months or less, 20 months or less, or 24 months or less from starting treatment with an anti-CTGF antibody.

An effective amount of an anti-CTGF antibody also refers to the amount of an anti-CTGF antibody that is sufficient to produce an extension in the median progression-free survival or median overall survival of IPF subjects treated with an anti-CTGF antibody over the survival seen in IPF subjects that are not treated with an anti-CTGF antibody. In some embodiments, the extension in median progression-free survival or median overall survival is produced with the administration of only an anti-CTGF antibody, while in other embodiments, the extension in either type of survival is produced through the combined treatment with an anti-CTGF antibody and one or more conventional treatments. In some embodiments, the extension in median progression-free survival or median overall survival is at least two weeks, 1 month, 2 months, 3 months, 4 months, 5 months, 6 months, 7 months, 8 months, 10 months, 12 months, 14 months, 16 months, 18 months, 20 months, 24 months, 28 months, 32 months, 36 months, 40 months, or 48 months beyond the median progression-free survival or median overall survival of conventionally treated IPF patients, i.e., treated with corticosteroids and/or immunosuppressive drugs or historic controls, e.g., placebo treated. In particular embodiments, an effective amount of an anti-CTGF antibody produces a 5-year survival rate of at least 30%, 35%, 40%, 45% or 50%.

Further, an effective amount of an anti-CTGF antibody also refers to the amount of an anti-CTGF antibody that is sufficient to decrease the risk of death due to IPF. In some embodiments, treatment with an effective amount of an anti-CTGF antibody reduces the 1-year risk, 2-year risk, 3-year risk, 4-year risk, 5-year risk, or 10-year risk of death by at least 5%, 10%, 15%, 20%, 25%, 30%, 35%, 40%, 50%, 60%, 70%, 80%, or 90% compared to conventionally treated subjects or historic controls, i.e., placebo treated.

An effective amount of an anti-CTGF antibody additionally refers to the amount of an anti-CTGF antibody that is sufficient to produce one or more of the following: (i) the prevention of a worsening of dyspnea; (ii) the prevention of the development of new dyspnea; (iii) the reduction in the frequency or intensity of coughing; (iv) the prevention of a worsening of hypoxemia; (v) the reduction in the number or severity of acute exacerbations of IPF; (vi) the reduction in the number of respiratory-related hospital admissions; (vii) the reduction in the need for supplemental oxygen; (viii) the reduction in days of disability; or (ix) the improvement in the assessment of health-related quality of life (QoL). In particular embodiments, an effective amount on an anti-CTGF antibody reduces the frequency or intensity of coughing, reduces the number or severity of acute exacerbations of IPF, reduces the number of respiratory-related hospital admissions, reduces the need for supplemental oxygen and/or reduces the number of days of disability by at least 5%, 10%, 15%, 20%, 25%, 30%, 35%, 40%, 45%, 50%, 55%, 60%, 65%, 70%, 75%, 80%, 85%, 90%, or 95% compared to conventionally treated subjects or historic controls, i.e., placebo treated.

A "prophylactically effective amount" is the amount of an anti-CTGF antibody that can prevent the onset of one or more symptoms or functional impairments associated with IPF. In some embodiments, a prophylactically effective amount of an anti-CTGF antibody is the amount that is effective in preventing a pathological rate of decline in one or more pulmonary function parameters. In other embodiments, a prophylactically effective amount of an anti-CTGF antibody is the amount that is effective in preventing the appearance of one or more pulmonary radiographic parameters.

Prophylactic administration is warranted in subjects that are at risk for developing IPF including former and current smokers and subjects that are genetically predisposed to the development of IPF, including those subjects that have a family history of IPF. A prophylactically effective amount of an anti-CTGF antibody used to prevent the onset of one or more symptoms of IPF can be the same amount or a different amount from a therapeutically effective amount of an anti-CTGF antibody. In some embodiments, the prophylactically effective amount of an anti-CTGF antibody is less than the therapeutically effective amount.

In some embodiments, the combination therapy of an anti-CTGF antibody with one or more other agents provides a synergistic improvement in therapeutic efficacy relative to the individual therapeutic agents when administered alone. The term "synergy" is used to describe a combined effect of two or more active agents that is greater than the sum of the individual effects of each respective active agent. Thus, where the combined effect of two or more agents results in "synergistic inhibition" of an activity or process, it is intended that the inhibition of the activity or process is greater than the sum of the inhibitory effects of each respective active agent. The term "synergistic therapeutic effect" refers to a therapeutic effect observed with a combination of two or more therapies wherein the therapeutic effect (as measured by any of a number of parameters) is greater than the sum of the individual therapeutic effects observed with the respective individual therapies.

By using the term "isolated" to describe an isolated antibody, antibody fragment, or antibody mimetic, it is intended that the molecule is not in its natural milieu. No particular level of purification is required. Recombinantly produced molecules are considered isolated for purposes of the invention, as are native molecules, e.g., polyclonal antibodies, that have been separated, fractionated, or partially or substantially purified by any suitable technique.

As used herein, "connective tissue growth factor" and "CTGF" refer to a matricellular protein belonging to a family of proteins identified as CCN proteins (Cysteine-rich 61 (Cyr61), Connective tissue growth factor (CTGF), Nephroblastoma overexpressed (Nov)). This family contains six distinct members (CYR61 (CCN1). CTGF (CCN2), NOV (CCN3), WISP-1 (wnt-1 inducible secreted protein-1, CCN4), WISP-2 (CCN5), and WISP-3 (CCN6)) that share a high degree of amino acid sequence homology. (See, e.g., O'Brian et al. (1990) *Mol Cell Biol* 10:3569-3577; Joliot et al. (1992) *Mol Cell Biol* 12:10-21; Ryseck et al. (1991) *Cell Growth and Diff* 2:225-233; Simmons et al. (1989) *Proc Natl Acad Sci USA* 86:1178-1182; Pennica et al. (1998) *Proc Natl Acad Sci USA*, 95:14717-14722; and Zhang et al. (1998) *Mol Cell Biol* 18:6131-6141.)

CTGF may also be referred to within the art as "hypertrophic chondrocyte-specific protein 24," "insulin-like growth factor-binding protein," and "CCN2." "CTGF" further refers to a substantially purified CTGF derived from any species, particularly a mammalian species, including rat, rabbit, bovine, ovine, porcine, murine, equine, and hominid, preferably the human species, and from any source, whether natural, synthetic, semi-synthetic, or recombinant.

Although the present invention demonstrates that agents that inhibit CTGF activity are beneficial in treating IPF and/or ameliorating one or more symptoms of IPF, the invention specifically contemplates the inhibition of the activity of other CCN family members, particularly Cyr61. In some embodiments, an antibody against Cyr61 is administered to an IPF patient for the purpose of curing or ameliorating one or more symptoms of IPF.

Antibodies

The term "antibody" is used in the broadest sense and specifically covers monoclonal antibodies (including full length monoclonal antibodies), polyclonal antibodies, multispecific antibodies (e.g., bispecific antibodies), and antibody fragments, so long as they exhibit the desired biological activity, and antibody mimetics.

The term "monoclonal antibody" as used herein refers to an antibody obtained from a population of substantially homogeneous antibodies, i.e., the individual antibodies comprising the population are identical except for possible mutations, e.g., naturally occurring mutations, that may be present in minor amounts. Thus, the modifier "monoclonal" indicates the character of the antibody as not being a mixture of discrete antibodies. In certain embodiments, such a monoclonal antibody typically includes an antibody comprising a polypeptide sequence that binds a target, wherein the target-binding polypeptide sequence was obtained by a process that includes the selection of a single target binding polypeptide sequence from a plurality of polypeptide sequences. For example, the selection process can be the selection of a unique clone from a plurality of clones, such as a pool of hybridoma clones, phage clones, or recombinant DNA clones. It should be understood that a selected target binding sequence can be further altered, for example, to improve affinity for the target, to humanize the target binding sequence, to improve its production in cell culture, to reduce its immunogenicity in vivo, to create a multispecific antibody, etc., and that an antibody comprising the altered target binding sequence is also a monoclonal antibody of this invention. In contrast to polyclonal antibody preparations, which typically include different antibodies directed against different determinants (epitopes), each monoclonal antibody of a monoclonal antibody preparation is directed against a single determinant on an antigen.

The modifier "monoclonal" indicates the character of the antibody as being obtained from a substantially homogeneous population of antibodies, and is not to be construed as requiring production of the antibody by any particular method. For example, the monoclonal antibodies to be used in accordance with the present invention may be made by a variety of techniques, including, for example, the hybridoma method (e.g., Kohler and Milstein, Nature, 256:495-97 (1975); Harlow et al., Antibodies: A Laboratory Manual (Cold Spring Harbor Laboratory Press, 2nd ed. 1988); recombinant DNA methods (see, e.g., U.S. Pat. No. 4,816, 567); phage-display technologies (see, e.g., Clackson et al., Nature, 352: 624-628 (1991); Marks et al., J Mol Biol 222: 581-597 (1992); and Lee et al., J Immunol Methods 284(1-2): 119-132(2004)), and technologies for producing human or human-like antibodies in animals that have parts or all of the human immunoglobulin loci or genes encoding human immunoglobulin sequences (see, e.g., WO 1998/24893; WO 1996/34096; WO 1996/33735; WO 1991/10741; Jakobovits et al., Proc Natl Acad Sci USA 90: 2551 (1993); U.S. Pat. Nos. 5,545,807; 5,545,806; 5,569,825; 5,625,126; 5,633, 425; and 5,661,016).

Monoclonal antibodies specifically include "chimeric" antibodies in which a portion of the heavy and/or light chain is identical with or homologous to corresponding sequences in antibodies derived from a particular species or belonging to a particular antibody class or subclass, while the remainder of the chain(s) is identical with or homologous to corresponding sequences in antibodies derived from another species or belonging to another antibody class or subclass (see, e.g., U.S. Pat. No. 4,816,567; and Morrison et al., Proc Natl Acad Sci USA 81:6851-6855 (1984)).

"Humanized" forms of non-human (e.g., murine) antibodies are chimeric antibodies that contain minimal sequence derived from non-human immunoglobulin. In some embodiments, a humanized antibody is a human immunoglobulin (recipient antibody) in which residues from a one or more hypervariable regions (HVRs) of the recipient are replaced by residues from one or more HVRs of a non-human species (donor antibody) such as mouse, rat, rabbit, or nonhuman primate having the desired specificity, affinity, and/or capacity. For further details, see, e.g., Jones et al., Nature 321:522-525 (1986); Riechmann et al., Nature 332:323-329 (1988); and U.S. Pat. Nos. 6,982,321 and 7,087,409.

A "human antibody" is one which possesses an amino acid sequence which corresponds to that of an antibody produced by a human and/or has been made using any of the techniques for making human antibodies (see e.g., Hoogenboom and Winter, J. Mol. Biol., 227:381 (1991); Marks et al., J. Mol Biol., 222:581 (1991); Boerner et al., J. Immunol., 147(1):86-95 (1991); Li et al., Proc. Natl. Acad. Sci. USA, 103:3557-3562 (2006) and U.S. Pat. Nos. 6,075,181 and 6,150,584).

A "naked antibody" for the purposes herein is an antibody that is not conjugated to a cytotoxic moiety or radiolabel. In some embodiments, the anti-CTGF antibody is a naked antibody.

The anti-CTGF antibodies of the invention may be specific for CTGF endogenous to the species of the subject to be treated or may be cross-reactive with CTGF from one or more other species. In some embodiments, the antibody for use in the present methods is obtained from the same species as the subject in need. In other embodiments, the antibody is a chimeric antibody wherein the constant domains are obtained from the same species as the subject in need and the variable domains are obtained from another species. For example, in treating a human subject the antibody for use in the present methods may be a chimeric antibody having constant domains that are human in origin and variable domains that are mouse in origin. In preferred embodiments, the antibody for use in the present methods binds specifically to the CTGF endogenous to the species of the subject in need. Thus, in certain embodiments, the antibody is a human or humanized antibody, particularly a monoclonal antibody, that specifically binds human CTGF (GenBank Accession No. NP_001892).

Exemplary antibodies for use in the IPF treatment methods of the present invention are described, e.g., in U.S. Pat. No. 5,408,040; PCT/US1998/016423; PCT/US1999/029652 and International Publication No. WO 99/33878. Preferably, the anti-CTGF antibody for use in the IPF treatment method is a monoclonal antibody. Preferably the antibody is a neutralizing antibody. In particular embodiments, the antibody is the antibody described and claimed in U.S. Pat. Nos. 7,405,274 and 7,871,617. In some embodiments, the antibody for treatment of IPF has the amino acid sequence of the antibody produced by the cell line identified by ATCC Accession No. PTA-6006. In other embodiments, the antibody binds to CTGF competitively with an antibody produced by ATCC Accession No. PTA-6006. In further embodiments, the antibody binds to the same epitope as the antibody produced by ATCC Accession No. PTA-6006. A particular antibody for use in the IPF treatment methods is CLN1 or mAb1 as described in U.S. Pat. No. 7,405,274, or an antibody substantially equivalent thereto or derived therefrom. In some embodiments, the anti-CTGF antibody is CLN1, an antibody identical to the antibody produced by the cell line identified by ATCC Accession No. PTA-6006 that is encompassed by the claims of U.S. Pat. Nos. 7,405,274 and 7,871,617.

As referred to herein, the phrase "an antibody that specifically binds to CTGF" includes any antibody that binds to CTGF with high affinity. Affinity can be calculated from the following equation:

$$\text{Affinity} = K_a = \frac{[Ab \cdot Ag]}{[Ab][Ag]} = \frac{1}{K_d}$$

where [Ab] is the concentration of the free antigen binding site on the antibody, [Ag] is the concentration of the free antigen, [Ab·Ag] is the concentration of occupied antigen binding sites, $K_a$ is the association constant of the complex of antigen with antigen binding site, and $K_d$ is the dissociation constant of the complex. A high-affinity antibody typically has an affinity at least on the order of $10^8$ $M^{-1}$, $10^9$ $M^{-1}$ or $10^{10}$ $M^{-1}$. In particular embodiments, an antibody for use in the present methods will have a binding affinity for CTGF between of $10^8$ $M^{-1}$ and $10^{10}$ $M^{-1}$, between $10^8$ $M^{-1}$ and $10^9$ $M^{-1}$ or between $10^8$ $M^{-1}$ and $10^{10}$ $M^{-1}$. In some embodiments the high-affinity antibody has an affinity of about $10^8$ $M^{-1}$, $10^9$ $M^{-1}$ or $10^{10}$ $M^{-1}$.

"Antibody fragments" comprise a functional fragment or portion of an intact antibody, preferably comprising an antigen binding region thereof. A functional fragment of an antibody will be a fragment with similar (not necessarily identical) specificity and affinity to the antibody which it is derived. Non-limiting examples of antibody fragments include Fab, F(ab')$_2$, and Fv fragments that can be produced through enzymatic digestion of whole antibodies, e.g., digestion with papain, to produce Fab fragments. Other non-limiting examples include engineered antibody fragments such as diabodies (Holliger P et al. *Proc Natl Acad Sci USA*. 1993, 90: 6444-6448); linear antibodies (Zapata et al. 1995 *Protein Eng*, 8(10):1057-1062); single-chain antibody molecules (Bird K D ct al. *Science*, 1988, 242: 423-426); single domain antibodies, also known as nanobodies (Ghahoudi M A et al. *FEBS Lett*. 1997, 414: 521-526); domain antibodies (Ward E S et al. *Nature*. 1989, 341: 544-546); and multispecific antibodies formed from antibody fragments.

Antibody Mimetics

Antibody mimetics are proteins, typically in the range of 3-25 kD, that are designed to bind an antigen with high specificity and affinity like an antibody, but are structurally unrelated to antibodies. Frequently, antibody mimetics are based on a structural motif or scaffold that can be found as a single or repeated domain from a larger biomolecule. Examples of domain-derived antibody mimetics include AdNectins that utilize the 10th fibronectin III domain (Lipovšek D. *Protein Eng Des Sel*, 2010, 24:3-9); Affibodies that utilize the Z domain of *staphylococcal* protein A (Nord K et al. *Nat Biotechnol*. 1997, 15: 772-777), and DARPins that utilize the consensus ankyrin repeat domain (Amstutz P. *Protein Eng Des Sel*. 2006, 19:219-229). Alternatively, antibody mimetics can also be based on the entire structure of a smaller biomolecule, such as Anticalins that utilize the lipocalin structure (Beste G et al. *Proc Natl Acad Sci USA*. 1999, 5:1898-1903). In some embodiments, the anti-CTGF antibody is an antibody mimetic.

Pharmaceutical Compositions

The anti-CTGF antibodies, including antibody fragments and antibody mimetics, used in the methods of the present invention can be delivered directly or in pharmaceutical compositions containing carriers and/or excipients, as is well known in the art. The anti-CTGF antibodies may be administered intravenously as a bolus or by continuous infusion over a period of time. Alternately, the anti-CTGF antibodies may be administered by intramuscular, subcutaneous, intradermal, subdermal or intraperitoneal injection, topical administration, oral administration or by inhalation. The route of administration may influence the type and composition of the formulation used in the anti-CTGF antibody preparation. Pharmaceutical compositions of particular interest include compositions suitable for injectable use and compositions suitable for nebulization or aerosolization.

The composition can be a liquid solution, suspension, emulsion, tablet, pill, capsule, sustained release formulation, powder, or lyophilized cake. Injectable forms include sterile aqueous solutions, dispersions and sterile powders for the extemporaneous preparation of sterile injectable solutions or dispersions.

Anti-CTGF antibody formulations for use in accordance with the present invention may be prepared by mixing an anti-CTGF antibody with pharmaceutically acceptable carriers, excipients or stabilizers that are nontoxic to subjects at the dosages and concentrations employed. Anti-CTGF antibody formulations may include buffers such as phosphate, citrate, and other organic acids; antioxidants including ascorbic acid and methionine; preservatives such as octadecyldimethylbenzyl ammonium chloride, hexamethonium chloride, benzalkonium chloride, benzethonium chloride, phenol, or benzyl alcohol; alkyl parabens including methyl or propyl paraben, catechol, resorcinol, cyclohexanol, 3-pentanol, and m-cresol; carriers; hydrophilic polymers such as polyvinylpyrrolidone; monosaccharides, disaccharides, and other carbohydrates including glucose, mannose, or dextrins; chelating agents such as EDTA; sugars such as sucrose, mannitol, trehalose or sorbitol; salt-forming counter-ions such as sodium; metal complexes; and/or non-ionic surfactants or polyethylene glycol.

In particular, anti-CTGF antibody formulations may further comprise low molecular weight polypeptides; carriers such as serum albumin, gelatin, or immunoglobulins; and amino acids such as glycine, glutamine, asparagine, histidine, arginine, or lysine. The anti-CTGF antibody formulations can be lyophilized as described in PCT/US1996/012251. Additionally, sustained-release preparations may also be prepared. Frequently, polymers such as poly(lactic acid), poly(glycolic acid), or copolymers thereof serve as controlled/sustained release matrices, in addition to others well known in the art.

Numerous other pharmaceutically acceptable carriers, excipients, and stabilizers are available in the art, some of which are listed in various pharmacopoeias, e.g., US Pharmacopeia, Japanese Pharmacopeia, European Pharmacopeia, and British Pharmacopeia. Other sources include Gennaro, ed. (2000) *Remington's Pharmaceutical Sciences*, supra; and Goodman and Gilman's *The Pharmacological Basis of Therapeutics*, 10$^{th}$ Ed. (2001), Hardman, Limbird, and Gilman, eds. MacGraw Hill Intl.; the Inactive Ingredient Search database maintained by the FDA and the *Handbook of Pharmaceutical Additives*, ed. Ash, Synapse Information Resources, Inc., 3rd Ed. 2007.

Compositions formulated for parenteral administration by injection are usually sterile and can be presented in unit dosage forms, e.g., in ampoules, syringes, injection pens, or in multi-dose containers, the latter usually containing a preservative. In certain instances, such as with a lyophilized product or a concentrate, the parenteral formulation would be reconstituted or diluted prior to administration.

The anti-CTGF antibodies can be supplied or administered at any desired concentration. In some embodiments, the anti-CTGF antibody concentration is at least 1 mg/ml, 5 mg/ml, 10 mg/ml, 20 mg/ml, 25 mg/ml, 50 mg/ml, 75 mg/ml, 100 mg/ml, 125 mg/ml, 150 mg/ml, or 200 mg/ml. In other embodiments, the anti-CTGF antibody concentration is no more than about 5 mg/ml, 10 mg/ml, 20 mg/ml, 25 mg/ml, 50 mg/ml, 75 mg/ml, 100 mg/ml, 125 mg/ml, 150 mg/ml, 200 mg/ml, 250 mg/ml, or 300 mg/ml. In further embodiments, the anti-CTGF antibody concentration is between 5 mg/ml to 20 mg/ml, 20 mg/ml to 50 mg/ml, 50 mg/ml to 100 mg/ml, 100 mg/ml to 200 mg/ml, or 200 mg/ml to 300 mg/ml.

Dosage

A therapeutically effective amount of an anti-CTGF antibody can be administered in one or more administrations, applications or dosages. The skilled artisan will appreciate that certain factors may influence the dosage and timing required to effectively treat a subject, including but not limited to the severity or extent of the disease, the administration route, previous treatments, concurrent medications, performance status, weight, gender, race or ethnicity, and/or age of the subject.

In some embodiments, the method for treating IPF in a subject in need thereof comprises administering at least 0.5 g, at least 1.0 g, at least 1.5 g, at least 2.0 g, at least 2.5 g, or at least 3.0 g of an anti-CTGF antibody per a one, two, or three week period. In specific embodiments, the anti-CTGF antibody is administered at a dose of about 1.05 g or about 2.1 g every three weeks, based on a 70 kg standard man.

In a further embodiment, the method for treating IPF in a subject in need thereof comprises administering at least 10 mg/kg, 15 mg/kg, 20 mg/kg, 25 mg/kg, 30 mg/kg, 40 mg/kg, 50 mg/kg, or 60 mg/kg of an anti-CTGF antibody per a per a one, two, or three week period. In particular embodiments, the anti-CTGF antibody is administered at a dose of about 15 mg/kg or about 30 mg/kg every three weeks.

In some embodiments, a method for treating IPF presented herein involves the administration to a subject in need thereof of an anti-CTGF antibody at a dose that achieves a target plasma concentration of the anti-CTGF antibody in the subject. In some embodiments, the target plasma concentration of an anti-CTGF antibody is a maximum antibody concentration ($C_{max}$) in the plasma, typically seen immediately after i.v. administration to the subject. In particular embodiments, the method for treating IPF achieves a $C_{max}$ of at least 10 μg/ml, 50 μg/ml, 100 μg/mL, 200 μg/mL, 300 μg/mL, or 400 μg/mL.

In other embodiments, the target plasma concentration is a minimum antibody concentration ($C_{min}$) in the plasma, also known as a trough antibody concentration, that is typically measured immediately before a subsequent antibody administration to the subject. In some embodiments, the $C_{min}$ plasma concentration of the anti-CTGF antibody is at least 0.1 μg/ml, 1.0 μg/ml, 5 μg/ml, 10 μg/mL, 20 μg/ml, 30 μg/ml, 40 μg/ml, 50 μg/ml, 60 μg/ml, 70 μg/ml, 80 μg/ml, 90 μg/ml, 100 μg/ml, 125 μg/ml, 150 μg/ml, 200 μg/ml, 300 μg/ml, or 400 μg/ml. In further embodiments, $C_{min}$ is measured for a treatment cycle of about 2, 3, 4, 5, 6, 7, 8, 9, 10, 11, 12, 13, 14, 15, 16, 17, 18, 19, 20, 21, 22, 23, 24, or 28 days. In a particular embodiment, the $C_{min}$ is at least 10.0 μg/mL when measured at about 21 days after administration of an anti-CTGF antibody dose.

In further embodiments, a method for treating IPF in a subject in need thereof comprises the administration of an anti-CTGF antibody at a dose that achieves a target antibody exposure (area under the curve, AUC) over a specific time period. Typically, AUC is expressed as μg*h/ml. In some embodiments, a method for treating IPF in a subject in need thereof comprises the administration to a subject an anti-CTGF antibody at a dose that achieves an AUC in plasma of at least 1,000 μg*h/ml, 10,000 μg*h/ml, 25,000 μg*h/ml, 50,000 μg*h/ml, 60,000 μg*h/ml, 80,000 μg*h/ml, 100,000 μg*h/ml, 120,000 μg*h/ml, or 140,000 μg*h/ml. In some embodiments, the AUC is calculated from about 0-4 days, 0-5 days, 0-6 days, 0-7 days, 0-8 days, 0-9 days, 0-10 days, 0-11 days, 0-12 days, 0-13 days, 0-14 days, 0-16 days, 0-18 days 0-21 days, or 0-28 days. In a particular embodiment, the AUC is at least 1,000 μg*h/ml when measured from 0-21 days post-administration ($AUC_{0-21}$).

To achieve or exceed a desired plasma anti-CTGF antibody concentration, i.e., $C_{max}$, $C_{min}$, or AUC, an anti-CTGF antibody or a pharmaceutical composition thereof may be administered at a dose from 0.5 mg/kg to 60 mg/kg, i.e., 0.5 mg of an anti-CTGF antibody/kg patient body weight to 60 mg of an anti-CTGF antibody/kg patient body weight, depending upon the route of administration. In particular embodiments, a desired plasma anti-CTGF antibody concentration can be achieved or exceeded with an i.v. administration of a dose of at least 5 mg/kg, 10 mg/kg 15 mg/kg, 20 mg/kg, 25 mg/kg, 30 mg/kg, 35 mg/kg, 40 mg/kg, 45 mg/kg, 50 mg/kg, or 60 mg/kg. In specific embodiments, a desired plasma anti-CTGF antibody concentration can be achieved or exceeded with an administration of an anti-CTGF antibody at a dose of about 15 mg/kg or 30 mg/kg.

In some embodiments, the patient is treated for a minimum of 2 weeks, 3 weeks, 4 weeks, 6 weeks, 9 weeks, 12 weeks, 15 weeks, 18 weeks, 21 weeks, 24 weeks, 27 weeks, 30 weeks, 36 weeks, 40 weeks, 48 weeks, 1 year, or 2 years. In other embodiments, the patient is treated every 1 week, 2 weeks, 3 weeks, 4 weeks, 5 weeks, 6 weeks, 8 weeks, 10 weeks, or 12 weeks as indicated by the patient's healthcare practitioner. In additional embodiments, the patient is treated for a maximum of 6 weeks, 9 weeks, 12 weeks, 15 weeks, 18 weeks, 21 weeks, 24 weeks, 27 weeks, 30 weeks, 36 weeks, 40 weeks, 48 weeks, 1 year, 2 years, 3 years, 4 years, or 5 years. In further embodiments, the treatment duration is between 1 week to 24 weeks, 24 weeks to 48 weeks, 48 weeks to 2 years, 3 weeks to 2 years or 3 weeks to 3 years.

In some embodiments, the subject's anti-CTGF antibody plasma concentration is titrated, i.e., the anti-CTGF antibody dose may be adjusted so to achieve or exceed a target plasma concentration that is associated with a desired therapeutic response. In some embodiments, a method is provided for treating IPF in a subject in need thereof comprising: a) administering a first dose of an anti-CTGF antibody; b) measuring a first anti-CTGF antibody plasma concentration in the patient; c) comparing the first anti-CTGF antibody plasma concentration to a first target anti-CTGF antibody plasma concentration; and d) administering a second dose of the anti-CTGF antibody calculated to achieve or exceed the first target anti-CTGF antibody plasma concentration when a second measurement of anti-CTGF antibody plasma concentration is performed at substantially the same time interval post-administration as the measurement of the first antibody plasma concentration. In particular embodiments, the first target anti-CTGF antibody plasma concentration is 0.1 μg/ml, 1.0 μg/ml, 5 μg/ml, 10 μg/mL, 20 μg/mL, or 40 μg/mL when measured 21 days post-administration.

In some embodiments, the anti-CTGF antibody is administered at least two times with the first dose being a loading dose and the second and subsequent doses being maintenance doses. The term "loading dose" as used herein refers to an initial antibody dose administered within a set time period to rapidly achieve a desired therapeutic antibody concentration or associated therapeutic effect.

In some embodiments, the loading dose is at least 1 mg/kg, 5 mg/kg, 10 mg/kg, 12.5 mg/kg, 15 mg/kg, 20 mg/kg, 22.5 mg/kg, 25 mg/kg, 30 mg/kg, 35 mg/kg, 40 mg/kg, 45 mg/kg, 50 mg/kg, 55 mg/kg, 75 mg/kg, or 100 mg/kg. In other embodiments, the loading dose is the antibody dose that is sufficient to achieve an antibody concentration in plasma of at least 0.1 µg/ml, 1.0 µg/ml, 5 µg/ml, 10 µg/ml, 20 µg/ml, 25 µg/ml, 30 µg/ml, 40 µg/ml, 50 µg/ml, 60 µg/ml, 75 µg/ml, 75 µg/ml, 100 µg/ml, 125 µg/ml, 150 µg/m, or 200 µg/ml when measured about 21 days post-administration ($C_{min}$).

The term "maintenance dose" as used herein refers to an antibody dose sufficient to maintain a desired therapeutic antibody concentration or associated therapeutic effect that was achieved with the loading dose. For example, a maintenance dose may maintain a reduction, stabilization or reversal in the pathologic rate of decline in FVC that was achieved with a loading dose. Typically, the maintenance dose is lower than the loading dose.

In some embodiments, the maintenance dose is administered at least about 1, 2, 3, 4, 5, 6, 7, 8, 10, 12, 16, 20, or 24 weeks post-administration of the loading dose. In other embodiments, the maintenance dose is administered no more than about 1, 2, 3, 4, 5, 6, 7, 8, 10, 12, 16, 20, or 24 weeks post-administration of the loading dose. In further embodiments, the maintenance dose is administered within about 1 to 2 weeks, 1 to 3 weeks, 1 to 4 weeks, 1 to 6 weeks, 1 to 8 weeks, 2 to 10 weeks, 6 to 12 weeks, 10 to 20 weeks, or 12 to 25 weeks post-administration of the loading dose.

In some embodiments, the anti-CTGF antibody or a pharmaceutical composition comprising the antibody is administered through a bolus injection intravenously. In other embodiments, the anti-CTGF antibody is administered as an infusion that can be for a duration of not less than 10 minutes, 20 minutes, 30 minutes, 1 hour, 2 hours, 4 hours, or 8 hours. In further embodiments, the anti-CTGF antibody is administered subcutaneously in a concentrated form. In other embodiments, the anti-CTGF antibody is administered as an aerosolized powder or a nebulized solution for inhalation.

In specific embodiments, a method for treating IPF presented herein involves the administration to a subject in need thereof of an anti-CTGF antibody or a pharmaceutical composition thereof at a dosage and/or a frequency of administration that produces a functional outcome, e.g, reversal of decline in FVC. In other embodiments, a method for treating IPF presented herein involves the administration to a subject in need thereof of an anti-CTGF antibody or a pharmaceutical composition thereof at a dosage and/or a frequency of administration that produces an outcome that can be imaged such as a reduction or reversal in a pulmonary radiographic parameter or inflammation, as assessed by HRCT scan, chest x-ray, histopathologically, or another modality.

Subjects Suitable for Treatment

The methods of the invention are appropriate for the treatment of subjects diagnosed with IPF or UIP using any method recognized in the art including HRCT, chest x-rays, transbronchial biopsy and/or surgical lung biopsy. The methods of the invention are also appropriate for the treatment of subjects suspected of having IPF based on the presence of one or more characteristics known in the art to be indicative of the presence of IPF. These characteristics include progressive dyspnea and cough, bibasilar inspiratory crackles, digital clubbing, and non-specific bilateral, reticular infiltrates in the periphery of the lower lung zones visible on a chest radiograph. Further characteristics indicative of IPF include reduced lung volumes, a proportionate reduction in the pulmonary diffusing capacity or a normal to increased FEV1/FVC ratio demonstrated in pulmonary function tests. Other characteristics indicative of IPF include resting arterial blood hypoxemia, oxyhaemoglobin desaturation, or an increased alveolar-arterial oxygen pressure difference, any of which may worsen with exercise. Additional abnormalities during exercise that may indicate the presence of IPF include reduced peak oxygen consumption, diminished ventilatory reserve, high-frequency/low tidal volume breathing pattern, and high submaximal ventilation related in part to elevated physiologic dead space and arterial desaturation. A further characteristic indicative for IPF is the presence of pulmonary hypertension.

In some embodiments, one or more of the following pulmonary function parameters are used to select subjects for therapy with an anti-CTGF antibody or to monitor response to anti-CTGF antibody therapy: VC, FVC, FVC % predicted, RV, FEV, PEFR, IRV, FIF, FRC, IC, TLC, ERV, TV, or MVV. In particular embodiments, the pulmonary function parameters TLC, FVC, and FVC % predicted are used to select and/or monitor subjects.

Subjects that are particularly suited for treatment with the method of the invention are those that have a FVC % predicted value of at least 35%, 40%, 45%, 50%, 55%, 60%, 63%, 65%, 70%, 75%, 80%, 85%, 90%, or 95% of a normal person of similarly matched race or ethnicity, gender, age, height and weight. In other embodiments, subjects suitable for treatment with the method of the invention are those that have a FVC % predicted value of not more than 40%, 45%, 50%, 55%, 60%, 65%, 70%, 75%, 80%, 850%6, 90%, or 95%. In further embodiments, subjects suitable for treatment have a FVC % predicted value of between 40% to 95%, 50% to 90%, 55% to 85%, 60% to 80%, 55% to 80%, 60% to 70%, 70% to 90%, 60% to 90%, or 70% to 95%. In particular embodiments, the subjects have a FVC % predicted value of about 55%-85%.

Additional subjects that are particularly suited to treatment with the method of the invention are those that have at least 40%, 45%, 50%, 55%, 60%, 65%, 70%, 75%, 80%, 85%, 90%, or 95% of the predicted TLC of a normal person of similarly matched race or ethnicity, gender, age, height and weight. In other embodiments, subjects suitable for treatment with the method of the invention are those that have a not more than 40%, 45%, 50%, 55%, 60%, 65%, 70%, 75%, 80%, 85%, 90%, or 95% of the predicted TLC. In further embodiments, subjects suitable for treatment have between 40% to 95%, 45% to 90%, 50% to 85%, 55% to 85%, 50% to 70%, 60% to 80%, or 70% to 95% of the predicted TLC.

Further subjects that are particularly suited to treatment with the method of the invention are those that have at least 40%, 45%, 50/%, 55%, 60%, 65%, 70%, 75%, 80%, 85%, 90%, or 95% of the predicted FEV1 of a normal person of similarly matched race or ethnicity, gender, age, height and weight. In other embodiments, subjects suitable for treatment with the method of the invention are those that have a not more than 40%, 45%, 50%, 55%, 60%, 65%, 70%, 75%, 80%, 85%, 90%, or 95% of the predicted FEV1. In further embodiments, subjects suitable for treatment have between 40% to 95%, 45% to 90%, 50% to 85%, 55% to 85%, 50% to 70%, 60% to 80%, or 70% to 95% of the predicted FEV1.

In further embodiments, the subjects suitable for treatment with an anti-CTGF antibody have a pathologic rate of decline in one or more pulmonary function parameters of at least 5%, 10%, 15%, 20%, 30%, 40%, 50%, 60%, 70%, 80%, 90%, 100%, 125%, 150%, 200%, 300%, 400%, 500%, 600%, 700%, 800% or 1,000% over the expected rate of decline for a normal person of similarly matched race or ethnicity, gender, age, height and weight.

Subjects that are particularly suited for treatment with the method of the invention further include those that have a DLCO % predicted value corrected for blood hemoglobin of at least 25%, 30%, 35%, 40%, 45%, 50%, 55%, 60%, 65%, 70%, 75%, 80%, 85%, 90%, or 95%. In other embodiments, subjects suitable for treatment with the method of the invention are those that have a DLCO % predicted value corrected for blood hemoglobin of at least 25%, but not more than 40%, 45%, 50%, 55%, 60%, 65%, 70%, 75%, 80%, 85%, 90%, or 95%. In further embodiments, subjects suitable for treatment have a DLCO % predicted value corrected for blood hemoglobin between 30% to 95%, 40% to 90%, 45% to 85%, 50% to 90% or 60% to 80%.

Additional subjects that are particularly suited for treatment with the method of the invention are those that have a $SaO_2$ of at least 70%, 75%, 80%, 85%, 90%, 91%, 92%, 93%, 94%, 95%, 96%, 97%, 98%, or 99%. In other embodiments, subjects suitable for treatment with the method of the invention are those that have a $SaO_2$ of at least 70%, but not more than 80%, 85%, 90%, 91%, 92%, 93%, 94%, 95%, 96%, 97%, 98%, or 99%. In further embodiments, subjects suitable for treatment have a $SaO_2$ of between 70% to 95%, 70% to 99%, or 80% to 99%.

Other subjects that are particularly suited for treatment with the method of the invention are those that have a [A-a] $PO_2$ of at least 10 mmHg, 20 mmHg, 30 mmHg, 40 mmHg, 50 mmHg, 75 mmHg, 100 mmHg, 125 mmHg, 150 mmHg, 175 mmHg, 200 mmHg, or 250 mmHg. In other embodiments, subjects suitable for treatment have a [A-a] $PO_2$ between 10 mmHg to 50 mmHg, 10 mmHg to 100 mmHg, 10 mmHg to 200 mmHg, 20 mmHg to 250 mmHg, 50 mmHg to 250 mmHg, or 100 mmHg to 250 mmHg.

Further subjects that are particularly suited to treatment with the method of the invention are those subjects that are not more than 20 years old, 25 years old, 30 years old, 35 years old, 40 years old, 45 years old, 50 years old, 55 years old, 60 years old, 65 years old, 70 years old, 75 years old, 80 years old, 85 years old, or 90 years old. In other embodiments, subjects that are particularly suited to treatment with the method of the invention are those subjects that are not less than 20 years old, 25 years old, 30 years old, 35 years old, 40 years old, 45 years old, 50 years old, 55 years old, 60 years old, 65 years old, 70 years old, 75 years old, 80 years old, 85 years old, or 90 years old. In further embodiments, subjects that are particularly suited to treatment with the method of the invention are those subjects that are between 30 years old to 80 years old, 40 years old to 90 years old, 50 years old to 100 years old or 55 years old to 95 years old.

The methods are also suitable for the treatment of subjects with IPF who were previously treated with conventional therapies, including corticosteroids and/or immunosuppressive drugs, and failed to respond.

The methods of the invention are additionally suitable for subjects who are at risk of developing IPF. Those at risk include former and current smokers; those of the male gender; those with an age of 60 years or more; those with gastroesophageal reflux disease or those with a genetic predisposition for developing IPF.

Combination Therapy

In some embodiments, the methods for treating IPF provided herein involve administration of an anti-CTGF antibody in combination with one or more additional therapies. As used herein, the term "in combination" refers to the administration of the anti-CTGF antibody prior to, concurrent with, or subsequent to the administration of one or more additional therapies for use in treating IPF. The use of the term "in combination" does not restrict the order in which the anti-CTGF antibody and the one or more additional therapies are administered to a subject. The additional therapies may be administered by the same route or a different route of administration than used for the anti-CTGF antibody.

Current drug therapies for IPF include the administration of anti-inflammatories and immunosuppressives. Anti-inflammatory drugs include corticosteroids such as beclomethasone, betamethasone, budesonide, clobetasol, flunisolide, fluocinolone, fluocinonide, fluticasone, halobetasol, hydrocortisone, methylprednisolone, mometasone, prednisolone, prednisone, and triamcinolone. In some embodiments, the corticosteroid is administered as an aerosol, while, in other embodiments, the corticosteroid is administered orally. In particular embodiments, an anti-CTGF antibody is administered in combination with prednisone.

Anti-inflammatory drugs further include non-steroidal anti-inflammatories (NSAIDs) such as non-selective COX inhibitors and selective COX-2 inhibitors. Non-selective COX inhibitors include but are not limited to salicylic acid derivatives (e.g., aspirin, sodium salicylates, choline magnesium trisalicylate, salsalate, diflunisal, sulfasalazine, mesalamine and olsalazine), para-aminophenol derivatives (e.g., acetaminophen), indole and indene acetic acids (e.g., tolmetin, diclofenac, and ketorolac), heteroaryl acetic acids (e.g., abuprofen, flurbiprofen, ketoprofen, fenprofen, ibuprofen, naproxen, and oxaprozin), anthranilic acids or fenamates (e.g., mefenamic acid and meclofenamic acid), enolic acids (e.g., oxicams such as piroxicam and meloxicam), and alkanones (e.g., nabumetone). Selective COX-2 inhibitors include, but are not limited to, diaryl-substituted furanones (e.g., rofecoxib), diaryl-substituted pyrazoles (e.g., celecoxib), indole acetic acids (e.g., etodolac), and sulfonanilides (e.g., nimesulide).

In further embodiments, the methods of the invention include the administration of an anti-CTGF antibody in combination of with one or more TNF inhibitors that include, but are not limited to, etanercept (Enbrel®), adalimumab (HUMIRA®), or infliximab (Remicade®).

Examples of immunosuppressive drugs that can be administered in combination with anti-CTGF antibodies include, but are not limited to, methotrexate, cyclophosphamide, mizoribine, chlorambucil, cyclosporine, tacrolimus (FK506; ProGraf™), mycophenolate mofetil (CellCept®), azathioprine (6-mercaptopurine), sirolimus (rapamycin), deoxyspergualin, leflunomide, and its malononitriloamide analogs. In some embodiments, the anti-CTGF antibody is administered in combination with azathioprine. In other embodiments, one or more immunosuppressive drugs are administered as an aerosol. (See U.S. Pat. No. 8,158,110.)

In some embodiments, the anti-CTGF antibodies may be administered in combination with one or more antioxidants. Antioxidant agents include, but are not limited to, glutathione, taurine, niacin, and N-acetylcysteine (NAC). In particular embodiments, the anti-CTGF antibody is administered in combination with NAC. In further embodiments, the anti-CTGF antibodies may be administered in combination with one or more anti-fibrotic agents, including, but not limited to, colchicine, relaxin, halfuginone, suramin, prostaglandin E2, or d-penicillamine.

In further embodiments, an anti-CTGF antibody is administered in combination with at least one additional therapeutic agent selected from the group consisting of: pirfenidone (Esbriet®); intedanib (Vargatef®); an anti-(human monocyte chemoattractant protein-1) antibody, e.g., Carlumab; an anti-IL13 antibody, e.g., QAX-576, thalidomide; a c-Jun N-terminal kinase (JNK) inhibitor, e.g., CC-930; an anti-CD 20 antibody, e.g., Rituximab®, interferon-gamma 1b (Actimmune®); imatinib mesylate (Gleevac®); inhaled carbon monoxide; azathioprine; an anti-TGF-β antibody, e.g., GC1008; recombinant human serum amyloid P/pentraxin 2 (PRM-151); placental mesenchymal stem cells; minocycline; an anti-lysyl oxidase-like 2 (LOXL20) antibody, e.g., GS 6624; a 5-lipoxygenase inhibitor, e.g., Zileuton®; octreotide (Sandostatin®); a copper chelating agent (tetrathiomolybdate); an endothelin receptor antagonist, e.g., bosentan; a lysophosphatidic acid 1 (LPA1) receptor antagonist, e.g., AM152; and an angiotensin II receptor antagonist, e.g., Losartan®. Combination treatment further includes the aerosolized administration of an additional agent, such as interferon-γ (U.S. patent application Ser. No. 12/319,851).

In specific embodiments, the interval of time between the administration of an anti-CTGF antibody and the administration of one or more additional therapies may be about 0 to 15 minutes, 0 to 30 minutes, 30 minutes to 60 minutes, 1 to 2 hours, 2 to 6 hours, 2 to 12 hours, 12 to 24 hours, 1 to 2 days, 2 to 4 days, 4 to 7 days, 1 to 2 weeks, 2 to 4 weeks, 4 to 12 weeks, 12 to 24 weeks, or 24 to 52 weeks. In certain embodiments, an anti-CTGF antibody and one or more additional therapies are administered less than 1 day, 1 week, 2 weeks, 3 weeks, 4 weeks, one month, 2 months, 3 months, 6 months, or 1 year apart.

In certain embodiments, the anti-CTGF antibody is administered in combination with a medication for controlling or relieving symptoms associated with IPF. In some embodiments, the symptom associated with IPF is coughing, gastroesophageal reflux disease (GERD), weight loss, fatigue, or malaise. In further embodiments, the anti-CTGF antibody is administered in combination with pulmonary rehabilitation that may include exercise, nutritional counseling, smoking cessation counseling, psychological counseling, group counseling, breathing techniques, or techniques for conserving energy. In other embodiments, the anti-CTGF antibody is administered in combination with oxygen therapy or supplemental oxygen. In further embodiments, the anti-CTGF antibody is administered in combination with immunization to prevent influenza or pneumococcal infection.

In some embodiments, the interval of time between the administration of an anti-CTGF antibody and the administration of one or more supportive or symptomatic therapies may be about 0 to 15 minutes, 0 to 30 minutes, 30 minutes to 60 minutes, 1 to 2 hours, 2 to 6 hours, 2 to 12 hours, 12 to 24 hours, 1 to 2 days, 2 to 4 days, 4 to 7 days, 1 to 2 weeks, 2 to 4 weeks, 4 to 12 weeks, 12 to 24 weeks, or 24 to 52 weeks. In certain embodiments, an anti-CTGF antibody and one or more support or symptomatic therapies for IPF symptoms are administered less than 1 day, 1 week, 2 weeks, 3 weeks, 4 weeks, one month, 2 months, 3 months, 6 months, or 1 year apart.

In some embodiments, the administration of an anti-CTGF antibody and one or more additional therapies have an additive effect, while in other embodiments the combination of therapies have a synergistic effect. In specific embodiments, a synergistic effect of a combination therapy permits the use of lower dosages (e.g., sub-optimal conventional doses) of the additional therapy, e.g., prednisone. In other embodiments, the synergistic effect of a combination therapy allows for a less frequent administration of the additional therapy to a subject. In certain embodiments, the ability to utilize lower dosages of an additional therapy and/or to administer the additional therapy less frequently reduces the toxicity associated with the administration of the additional therapy, without reducing the efficacy of the additional therapy. In some embodiments, a synergistic effect results in improved efficacy of an anti-CTGF antibody and/or the additional therapies in treating IPF. In some embodiments, the treatment method reduces, stabilizes or reverses pulmonary fibrosis in a subject with IPF without producing the number or severity of adverse events that are associated with the use of corticosteroids or immunosuppressive agents.

The combination of an anti-CTGF antibody and one or more additional therapies can be administered to a subject in the same pharmaceutical composition. Alternatively, an anti-CTGF antibody and one or more additional therapies can be administered concurrently to a subject in separate pharmaceutical compositions. An anti-CTGF antibody and one or more additional therapies may also be administered to a subject by the same or different routes of administration.

Articles of Manufacture

The present compositions may, if desired, be presented in a pack or dispenser device containing one or more unit dosage forms containing the anti-CTGF antibody. Such a pack or device may, for example, comprise metal or plastic foil, glass and rubber stoppers, such as in vials, or syringes. The container holds or contains an anti-CTGF antibody composition that is effective for treating IPF and may have a sterile access port (for example the container may be an intravenous solution bag or a vial having a stopper pierceable by a hypodermic injection needle). The container holding the anti-CTGF antibody compositions may further be labeled for the treatment of IPF. The pack or dispenser device may be accompanied by instructions for administration including specific guidance regarding dosing amounts for the anti-CTGF antibody.

The article of manufacture may further comprise an additional container comprising a pharmaceutically acceptable diluent buffer, such as bacteriostatic water for injection (BWFI), phosphate-buffered saline, Ringer's solution, and/or dextrose solution. The article of manufacture may further include other materials desirable from a commercial and user standpoint, including other buffers, diluents, filters, needles, and syringes.

These and other embodiments of the present invention will readily occur to those of ordinary skill in the art in view of the disclosure herein.

EXAMPLES

The invention will be further understood by reference to the following examples, which are intended to be purely exemplary of the invention. The present invention is not limited in scope by the exemplified embodiments, which are intended as illustrations of single aspects of the invention only. Any methods that are functionally equivalent are within the scope of the invention. Various modifications of the invention in addition to those described herein will become apparent to those skilled in the art from the foregoing description and accompanying figures. Such modifications are intended to fall within the scope of the appended claims.

Example 1

A Phase I Study of Anti-CTGF Monoclonal Antibody CLN1 in Idiopathic Pulmonary Fibrosis A Phase I, open-label, single-dose, sequential-group, dose-escalation study of CLN1 was performed in 21 subjects with well-defined IPF. The subjects were Caucasians with a mean±SD age of 63±9 years (range, 42-79 years); and 76% were males. The mean duration of IPF at study entry was 571±608 days (range, 64-2893 days).

A human anti-CTGF antibody, CLN1, was infused intravenously over 2 hours at a dose of 1 mg/kg (n=6), 3 mg/kg (n=9), and 10 mg/kg (n=6). All doses of CLN1 were well tolerated with no infusion-related or dose-limiting toxicity observed. The subjects were monitored for safety for up to 1 year following administration where all doses of CLN1 demonstrated acceptable safety profiles.

Baseline pulmonary function parameter testing (TLC, RV, FVC, FEV1) and blood gas measurements (DLCO, [A-a] $PO_2$, and $SaO_2$) were performed days −15 to −4 pretreatment. (Table 1) Subjects demonstrated significantly compromised pulmonary function parameters with a pattern of restrictive ventilatory dysfunction with reduced gas transfer.

Following treatment with the anti-CTGF antibody, subjects were retested for pulmonary function parameters and blood gas measurements 28 days, 6 months and 1 year after treatment. No significant mean changes from baseline pulmonary function parameters were seen in any dose group 28 days post-treatment (Table 1). Further, 5 (23.8%) subjects had clinically significant negative changes in FVC values, defined as a decrease of >10% from baseline; and 3 (14.3%) had a >10% decrease in total lung capacity (TLC) values. No subjects had an increase in FVC or TLC values ≥10% within 28 days post-treatment. Additionally, no significant mean changes in blood gas measurements were seen in any dose group 28 days post-treatment (Table 1). In two (9.5%) subjects, DLCO decreased >10% from baseline. In three (14.3%) subjects, (A-a) $PO_2$ increased 12-16 mmHg from baseline to Day 28.

At the end of the 12-month follow-up period, 15 of the 21 (71.4%) subjects had completed the final 12-month protocol-specified assessments. Of the remaining six (28.6%) subjects, three had died from progressive disease, two had withdrawn consent, and one was withdrawn by the investigator because of worsening IPF, requiring bilateral lung transplant. Throughout the 6- and 12-month follow-up periods, the majority of subjects continued to display signs of disease progression including increased respiratory abnormalities and clinically significant changes in pulmonary function parameters and blood gas measurements.

Example 2

A Phase 2a, Open-Label, Single-Arm Study to Evaluate the Safety, Tolerability, and Efficacy of CLN1 in Subjects with Idiopathic Pulmonary Fibrosis Study Design The study is a Phase 2a, open-label, single-arm multicenter trial in subjects with moderate to severe IPF. The safety, tolerability, and efficacy of an anti-CTGF antibody (CLN1) at a dose of 15 mg/kg every 3 weeks were studied in 46 subjects that completed 12 weeks of treatment, 32 subjects that completed 24 weeks of treatment, and 15 subjects that completed 36 weeks of treatment.

The planned initial duration of a subject's participation is 60 weeks, including a screening period of up to 6 weeks, a 45-week treatment period, and a 9-week follow-up period. As the preliminary results demonstrated disease stabilization or reversal in a sub-population of subjects, the study was expanded to provide these responding subjects with the option to continue treatment for an additional year.

Eligible subjects, 35 to 80 years of age, required a clinical diagnosis of IPF as defined by the American Thoracic Society and European Respiratory Society international consensus statement (*Am J Respir Crit Care Med* (2000) 161: (2 Pt 1):646-664), along with one of the following: an HRCT scan obtained during screening that showed definite IPF, or an HRCT scan obtained during screening that was consistent

TABLE 1

Pulmonary function test results at baseline and Day 28

| Parameter | Time of Assessment | CLN1 Dose Group (mg/kg) | | |
|---|---|---|---|---|
| | | 1 (n = 6) | 3 (n = 9) | 10 (n = 6) |
| TLC (l) | Baseline | 4.23 (0.76) | 4.27 (1.29) | 4.30 (1.25) |
| | Day 28 | 4.14 (0.89) | 4.30 (1.25) | 4.14 (1.27) |
| TLC % of predicted value (%) | Baseline | 63.8 (13.7) | 67.4 (13.7) | 63.8 (14.6) |
| FVC (l) | Baseline | 2.58 (0.54) | 2.87 (1.05) | 2.76 (0.79) |
| | Day 28 | 2.45 (0.58) | 2.72 (1.03) | 2.81 (0.78) |
| FVC % of predicted value, % | Baseline | 61.7 (16.3) | 69.2 (16.0) | 60.5 (13.0) |
| $FEV_1$ (l) | Baseline | 2.09 (0.41) | 2.30 (0.72) | 2.15 (0.62) |
| | Day 28 | 2.01 (0.53) | 2.26 (0.78) | 2.12 (0.67) |
| $FEV_1$/FVC % | Baseline | 81.0 (8.3) | 81.8 (6.5) | 78.2 (8.7) |
| DLCO (mL/mmHg/min) | Baseline | 10.9 (2.0) | 11.4 (4.5) | 13.1 (3.1) |
| (corrected for Hgb) | Day 28 | 10.6 (1.8) | 11.2 (5.0) | 15.8 (4.8) |
| DLCO % of predicted value (%) | Baseline | 36.3 (9.2) | 38.1 (10.3) | 42.0 (14.1) |
| $SaO_2$ (%) | Baseline | 92.3 (5.5) | 93.4 (2.5) | 96.0 (1.3) |
| | Day 28 | 92.5 (5.9) | 92.8 (4.1) | 96.3 (2.0) |
| (A-a) $PO_2$ (mmHg) | Baseline | 24.0 (8.8) | 25.6 (18.6) | 48.8 (28.1) |
| | Day 28 | 20.8 (9.2) | 27.9 (16.1) | 38.3 (23.3) |

Data are presented as mean (standard deviation).
TLC: total lung capacity;
FVC: forced vital capacity;
$FEV_1$: forced expiratory volume in 1 second;
Hgb: haemoglobin;
DLCO: diffusing capacity of the lung for carbon monoxide;
$SaO_2$: arterial oxyhaemoglobin saturation;
(A-a) $PO_2$: alveolar-arterial oxygen tension gradient.

with IPF plus a surgical lung biopsy within 36 months prior to enrollment that showed definite usual interstitial pneumonia (UIP). The diagnosis of IPF needed to be ≤5 years' duration, and subjects needed to have evidence of progression of IPF within the 3 to 12 months preceding enrollment expressed as a worsening of disease based on HRCT scans, a decline in FVC % predicted by at least 10%, or other objective evidence of disease progression. Inclusion criteria further included the requirement of 10%-50% parenchymal fibrosis by HRCT; less than 25% honeycombing within the whole lung; a FVC % predicted of between 45%-85%; and a DLCO % predicted of greater than 30%.

Eligible subjects underwent an initial screening evaluation that included a review of each individual's medical history and available chest imaging studies. The screening evaluation further included a complete physical examination and baseline clinical laboratory measurements. Eligible subjects returned for a chest HRCT scan to determine if radiographic criteria for the extent of lung fibrosis were met. Subjects that remained eligible were enrolled into the study and began treatment. Subjects are monitored for safety after each infusion. Enrollment closed after 54 subjects were entered.

The initial anti-CTGF antibody dose (CLN1) was based on the Day 1 weight for the first 12 weeks. Subsequent doses of the anti-CTGF antibody were based on the first weight at the beginning of each subsequent 12-week period. The first administration of anti-CTGF antibody was given in no less than 2 hours. If the first administration was well tolerated and no drug-related adverse events (AEs) were observed during the infusion or subsequent 1-hour observation period, the second administration of the anti-CTGF antibody was given in no less than 1 hour. If the second administration was well tolerated and without drug-related AEs, all subsequent infusion periods were shortened to no less than half an hour.

Clinical laboratory tests to assess safety were performed at the first screening visit, at every visit for the first three infusions and then continued at 6-week intervals. Clinical laboratory tests are performed through Week 48. Efficacy parameters (pulmonary function parameters, blood gas measurements and patient reported outcomes (dyspnea and QoL)) are assessed at Weeks 12, 24, 36 and 48. Chest HRCT are obtained at Week 24 and Week 48.

Pulmonary function parameters were analyzed for change from baseline (determination of the rate of decline) in FVC, FVC % predicted, TLC, and FRC. DLCO was analyzed for change from baseline (determination of the rate of decline) in DLCO % or DLCO % predicted, adjusted for hemoglobin.

Follow-up HRCT scans at Week 24 were compared with the baseline HRCT scan by visual scoring ("better," "no change," "worse") in a blinded manner. The follow-up HRCT scans were also compared with the baseline HRCT scan through a CAD analysis scoring system (MedQIA, Los Angeles, Calif.) that is similar to that disclosed by Kim et al. (Kim et al. *Clin Exp Rheumatol.* (2010) 28(5 Suppl 62): S26-S35; Kim et al. *Eur Radiol* (2011) 21: 2455-2465). The percent change in three pulmonary radiographic parameters were measured: ground glass opacities, fibrosis and honeycomb formation by lung zone or lobe and also for the whole lung. Additionally, QILD was also calculated for each subject.

Data

A preliminary analysis of data is presented below. The data includes pulmonary function parameter data from 46 subjects who completed 12 weeks of treatment, 32 subjects who completed 24 weeks of treatment, and 15 subjects who completed 36 weeks of treatment. In addition, the data included baseline and 24-week HRCT scans from 12 subjects.

Disease severity at baseline, measured as FVC % predicted, ranged from 42.5 to 86.0%, with a median of 63.2%, n=47. Mean FVC was 2.61 L.

Subjects treated with an anti-CTGF antibody (CLN1) at 15 mg/kg every 3 weeks experienced a change in FVC from baseline at Week 12 post-initiation of therapy of −0.04 liters (n=46), the same as the change seen in IPF subjects from a composite placebo arm derived from recent IPF clinical trials, −0.04 liters. (Table 2.) At Week 24 post-initiation of therapy, the change in FVC from baseline was −0.09 liters (n=32) that again approximates the change seen in IPF subjects from the composite placebo arm derived from recent IPF clinical trials. At Week 36, the anti-CTGF antibody treated subjects demonstrated stabilization in the rate of the pathologic decline in FVC from baseline with a net change of −0.08 liters (n=15) from baseline compared with the extrapolated change of −0.12 liters seen in IPF subjects from the composite placebo arm derived from recent clinical trials.

TABLE 2

Change in FVC from baseline

| Interval | FVC Change from Baseline (liters) | | |
| --- | --- | --- | --- |
| | All Subjects | Baseline FVC % predicted >55% | Responders |
| Week 12 CLN1 | −0.04 N = 46 | 0.00 N = 34 | +0.05 N = 14 |
| Week 12 (historical placebos)* | −0.04 | | |
| Week 24 CLN1 | −0.09 N = 32 | −0.07 N = 26 | +0.06 N = 14 |
| Week 24 (historical placebos)* | −0.08 | | |
| Week 36 CLN1 | −0.08 N = 15 | −0.02 N = 12 | +0.04 N = 9 |
| Week 36 (historical placebos)* | −0.12 | | |

*IPF subjects in composite placebo arm derived from recent clinical trials, n = 1,122. Mean = approximately −0.16 liters at Week 48. (Richeldi L et al., *N Engl J Med* 2011; 365: 1079-1087; Noble PW et al., *Lancet* May 14, 2011 DOI: 10.1016/S0140-6736(11)60405-4; Azuma A et al. *Am J Respir Crit Care Med.* 2005 May 1; 171(9): 1040-47; Taniguchi H. et al. *Eur Respir J* 2010; 35: 821-829; Demedts M et al. *N Engl J Med* 2005; 353: 2229-2242; Raghu G et al. *N Engl J Med* 2004; 350: 125-133; King TE Jr et al, *Am J Respir Crit Care Med.* 2011 Jul 1; 184(1): 92-99; Daniels CE et al, *Am J Respir Crit Care Med.* 2010 Mar 15; 181(6): 604-10; Raghu G et al, *Am J Respir Crit Care Med.* 2008 Nov 1; 178(9): 948-55; Noth I et al. *Am J Respir Crit Care Med* 2012; 186: 88-95; Raghu G et al. *N Engl J Med* 2012; 366: 1968-1977)

An examination of the change in FVC (liters) from baseline at Week 24 and Week 36 post-initiation of therapy based on the subjects' baseline FVC % predicted value showed that overall, subjects with a higher baseline FVC % predicted value responded better to treatment. FIG. 1 The regression lines for changes in FVC vs. baseline FVC % predicted showed that subjects with a baseline FVC % predicted value of at least the median baseline value of 63% experienced a stabilization of disease or increase in FVC (reversal of the pathologic decline) at Week 24 and Week 36.

Figure 2:
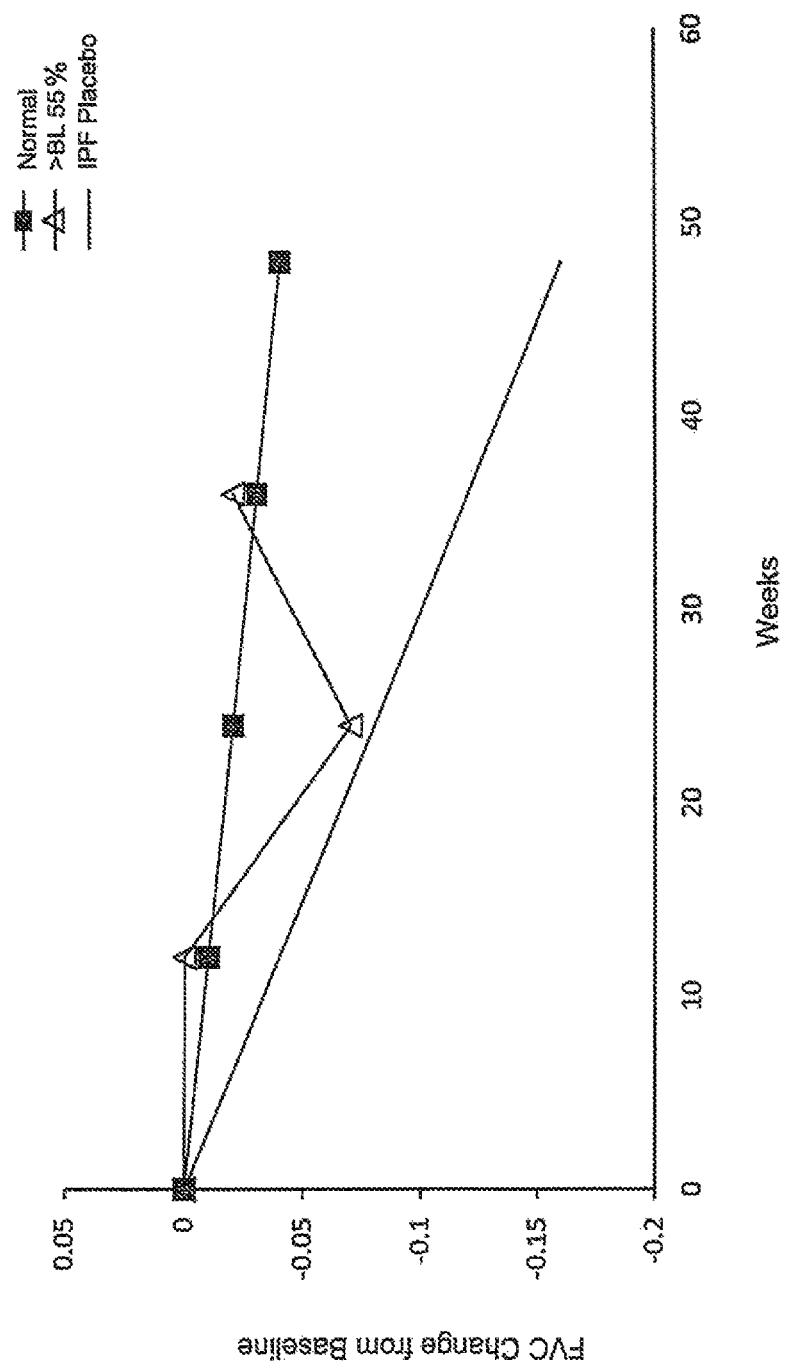
FIG. 2 illustrates the change in FVC (liters) from baseline over time in subjects treated with an anti-CTGF antibody that had a baseline FVC % predicted of at least 55% (>BL 55%). For comparison, the normal decline in FVC seen in a similarly matched normal population (Normal) is shown along with the pathologic decline in FVC of IPF patients in the composite placebo arm (IPF Placebo) derived from recent clinical trials, n=1,122. The anti-CTGF antibody treated subjects experienced a decline in FVC at Week 24 post-initiation of therapy that approached the decline seen in the IPF patients in the placebo arm. By Week 36 post-initiation of therapy, however, the anti-CTGF antibody treated subjects experienced an increase in FVC so that the overall decline for the anti-CTGF antibody treated subjects approximated that seen in the normal reference population. IPF patients in the placebo arm were calculated at Week 36 to have a −0.12 liter change from baseline and at Week 48 a −0.17 liter change from baseline.

An analysis of the change in FVC (in liters) from baseline of subjects treated with an anti-CTGF antibody that had a baseline FVC % predicted of at least 55% demonstrated that after approaching the change in FVC seen in IPF subjects at Week 24, there was an improvement in FVC at Week 36, a reversal in the pathologic rate of decline. FIG. 2 and Table 2

Figure 3:
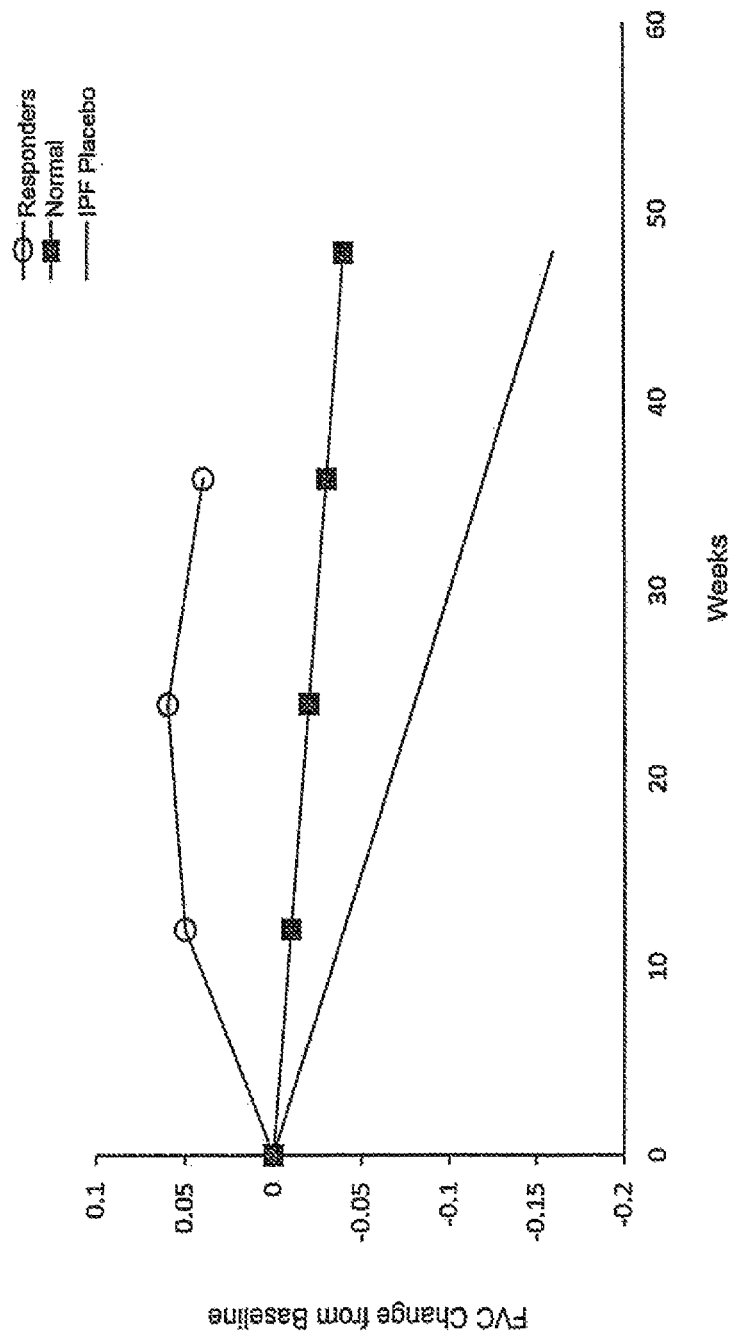
FIG. 3 illustrates the change in FVC (liters) from baseline over time in subjects that responded (Responders) to treatment with an anti-CTGF antibody. For comparison, the normal decline (Normal) seen in a similarly matched normal population is shown along with the pathologic decline in FVC of IPF patients in the composite placebo arm (IPF Placebo) derived from recent clinical trials, n=1,122. Responders demonstrated a gain in FVC across all time points for a net gain from baseline of about 0.04 liters at Week 36. IPF patients in the placebo arm were calculated at Week 36 to have a −0.12 liter change from baseline and at Week 48 a −0.17 liter change from baseline.

An examination of the change in FVC (in liters) from baseline in subjects that demonstrated an improvement (reversal in the pathologic decline) in FVC at Week 12 post-initiation of treatment with an anti-CTGF antibody revealed that the improvement in FVC persisted through Week 36 with a net gain in FVC of about 0.04 liters. FIG. 3 and Table 2 In contrast, the change in FVC for IPF subjects in the composite placebo arm derived from recent clinical trials was about −0.12 liters from baseline at Week 36.

Examination of another pulmonary function parameter, FVC % predicted, revealed that subjects treated with the anti-CTGF antibody (CLN1) at 15 mg/kg every 3 weeks experienced a change in FVC % predicted from baseline at Week 12 post-initiation of therapy of −0.80% (reduction in the pathologic rate of decline) compared to a change of −1.36% seen in subjects from the composite placebo arm derived from recent IPF clinical trials. Table 3 At Week 24 post-initiation of therapy, the change in FVC % predicted for subjects treated with an anti-CTGF antibody was −1.93% compared to a change of −2.73% for the subjects in the composite placebo arm derived from recent IPF clinical trials. At Week 36, the anti-CTGF antibody treated subjects had a change from baseline of −1.11% that demonstrates a reversal in the pathologic rate of decline in FVC % predicted compared to Week 24. In contrast, at Week 36 IPF subjects from the composite placebo arm had a change from baseline in FVC % predicted of −4.09%.

Inspection of results revealed that subjects treated with an anti-CTGF antibody that had a baseline FVC % predicted of at least 55% showed no appreciable change from baseline FVC % predicted at Week 12. Table 3 At Week 24, the change in FVC % predicted from baseline was −1.24%, later rebounding to +0.09% above baseline at Week 36, demonstrating a reversal in pathologic rate of decline of the FVC % predicted values for these subjects.

Surprisingly, at Week 12 about 30% of the subjects demonstrated a positive change in FVC % predicted from baseline. Table 3 These subjects with a mean+1.27% change in FVC % predicted were termed "responders" and demonstrate that treatment with an anti-CTGF antibody can reverse the pathological rate of decline in pulmonary function. The positive response was durable, lasting until at least Week 36.

TABLE 3

Change in FVC % predicted from baseline.

| | FVC % Predicted Change from Baseline | | |
|---|---|---|---|
| Interval | All Subjects | Baseline FVC % predicted >55% | Responders |
| Week 12 CLN1 | −0.80% N = 46 | +0.02% N = 34 | +1.27% N = 14 |
| Week 12 (historical placebos)* | −1.36% | | |
| Week 24 CLN1 | −1.93% N = 32 | −1.24% N = 26 | +1.71% N = 14 |
| Week 24 (historical placebos)* | −2.73% | | |
| Week 36 CLN1 | −1.59% N = 15 | +0.09% N = 12 | +1.43% N = 9 |
| Week 36 (historical placebos)* | −4.09% | | |

*IPF subjects in composite placebo arm derived from recent clinical trials, n = 1,019. Mean FVC % predicted change from baseline = −5.46% at Week 48. (Richeldi L et al., *N Engl J Med* 2011; 365: 1079-1087; Noble PW et al., *Lancet* May 14, 2011 DOI: 10.1016/S0140-6736(11)60405-4; Demedts M et al. *N Engl J Med* 2005; King TE Jr et al, *Lancet* 2009; 374: 222-2228; 353: 2229-2242; Raghu G et al. *N Engl J Med* 2004; 350: 125-133; Zisman DA et al. *N Engl J Med* 2010; 363: 620-628; Noth I et al. *Am J Respir Crit Care Med* 2012; 186: 88-95)

Figure 4:
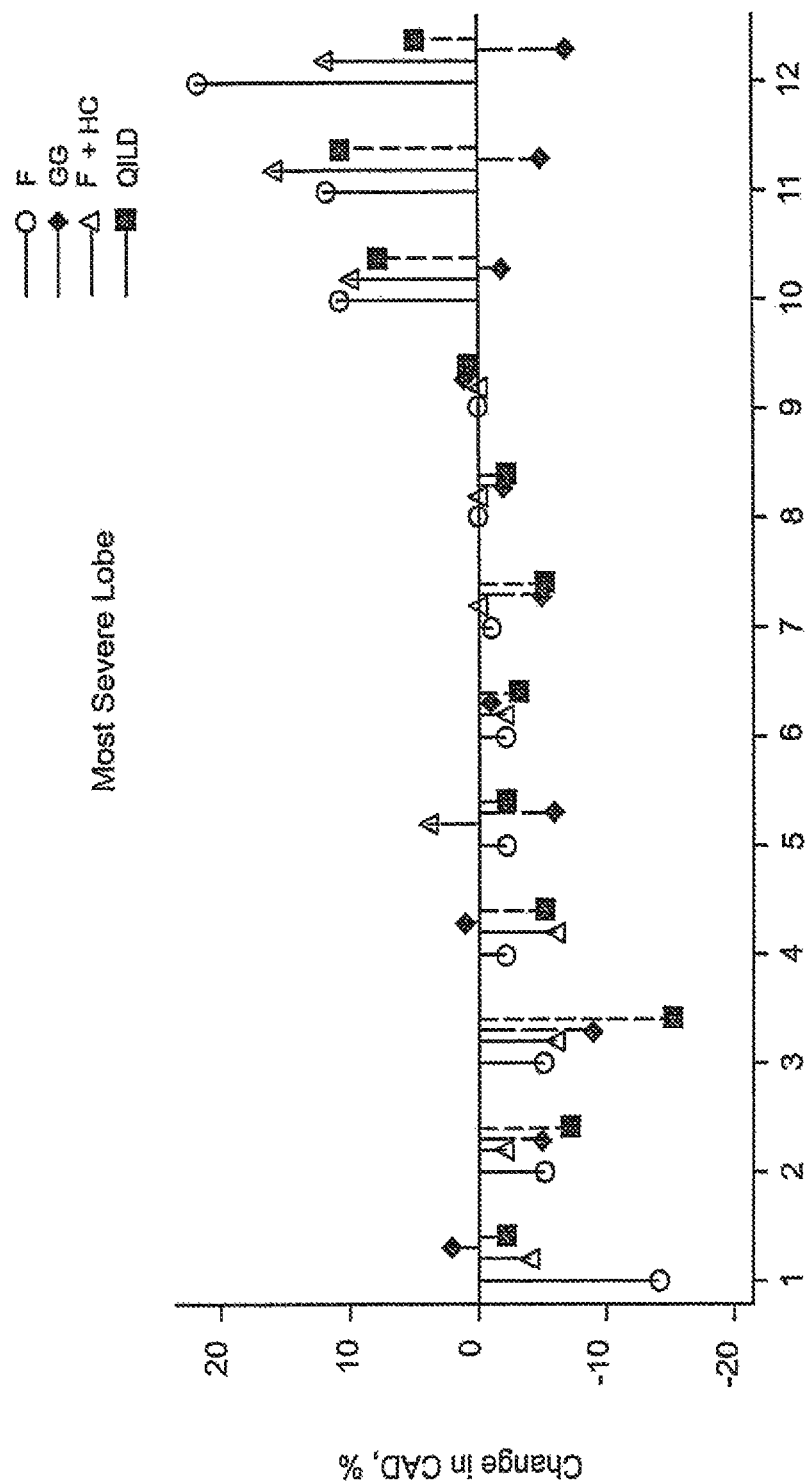
FIG. 4 illustrates the percent change in the extent of pulmonary fibrosis from baseline in the most severe lung lobe at Week 24 of subjects with IPF that were treated with an anti-CTGF antibody, n=12. HRCT scans were examined using a computer-aided detection (CAD) analysis system that measured three pulmonary radiographic parameters: ground glass opacities (GG), fibrosis (F) and honeycomb formation (HC). Subjects are ordered from left to right along the x-axis according to the extent of change in the mean CAD analysis fibrotic (F) score with subjects demonstrating the greatest reductions in fibrosis arranged on the left hand side. Also included is the measurement of total lung disease termed quantitative interstitial lung disease (QILD) that is the summation of a subject's GG, F and HC values. Half of the subjects demonstrated measurable improvement (reversal, <−2% change) in these pulmonary radiographic parameters while a quarter of the subjects demonstrated stable disease (±2% change in pulmonary radiographic parameters). Most subjects showed a reversal in the extent of ground glass opacities.
Figure 5:
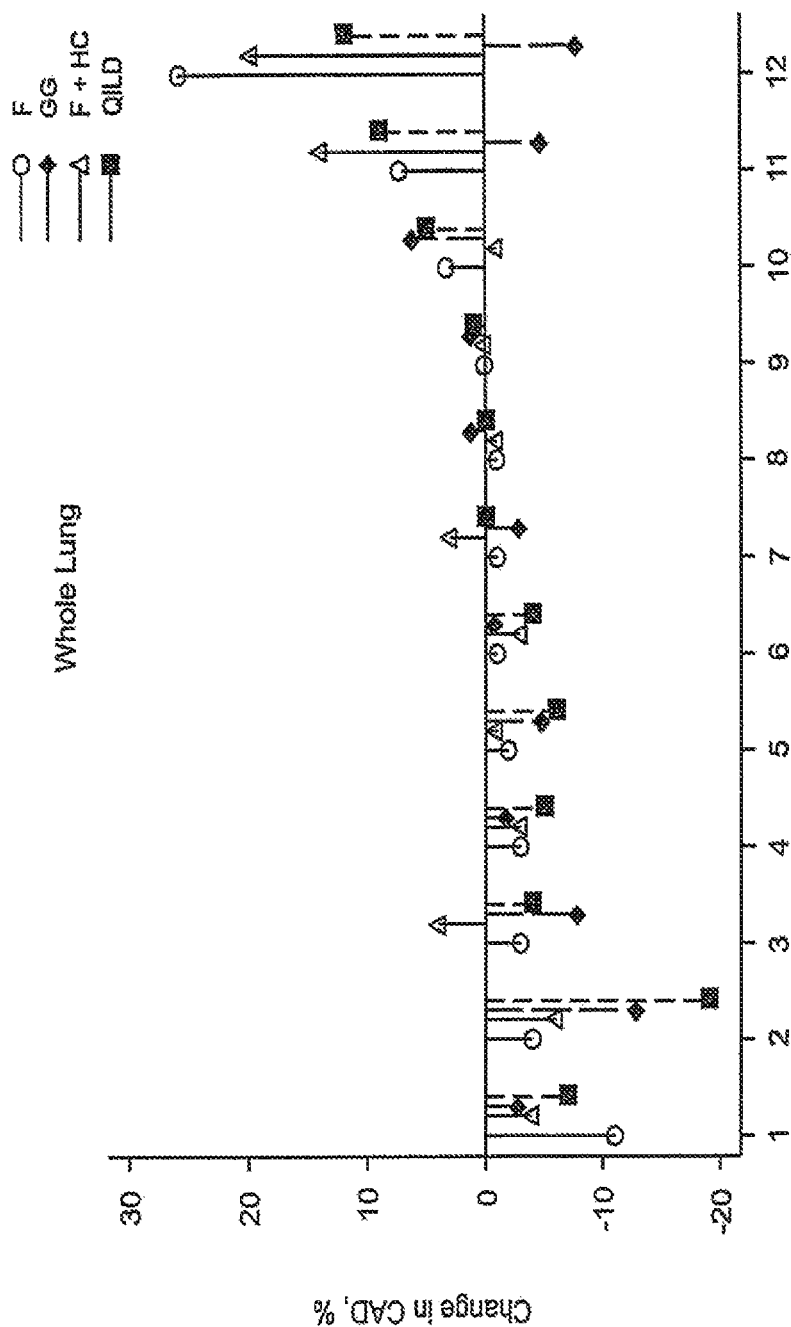
FIG. 5 illustrates the percent change in the extent of pulmonary fibrosis from baseline in whole lung at Week 24 of subjects with IPF that were treated with an anti-CTGF antibody, n=12. HRCT scans were examined using a CAD analysis system that measured three pulmonary radiographic parameters: GG, F and HC. Subjects retained the ordering from FIG. 4. Additionally, QILD values are shown. Half of the subjects demonstrated measurable improvement (reversal, <−2% change) in these pulmonary radiographic parameters, while a quarter of the subjects demonstrated stable disease (±2% pulmonary radiographic parameters). Most subjects showed a reversal in the extent of ground glass opacities.

HRCT scans from 12 subjects at Week 24 were compared to their respective baseline HRCT scan to assess changes in pulmonary fibrosis of individual lung lobes or the whole lung using CAD analysis. Three pulmonary radiographic parameters were examined: ground glass opacities, fibrosis and honeycomb formation. Additionally, QILD was also determined. About half of the subjects demonstrated a reversal in the extent of two or more pulmonary radiographic parameters in both the most severe lung lobe (FIG. 4) and whole lung (FIG. 5). About a quarter of the subjects appeared to have stable disease based on both the most severe lung lobe and whole lung CAD analysis. The direction and extent of change in the pulmonary radiographic parameters between the most severe lung lobe and the whole lung were similar for individual subjects. These data represent the first demonstration of a reversal in the extent of pulmonary fibrosis in IPF subjects.

Figure 6:
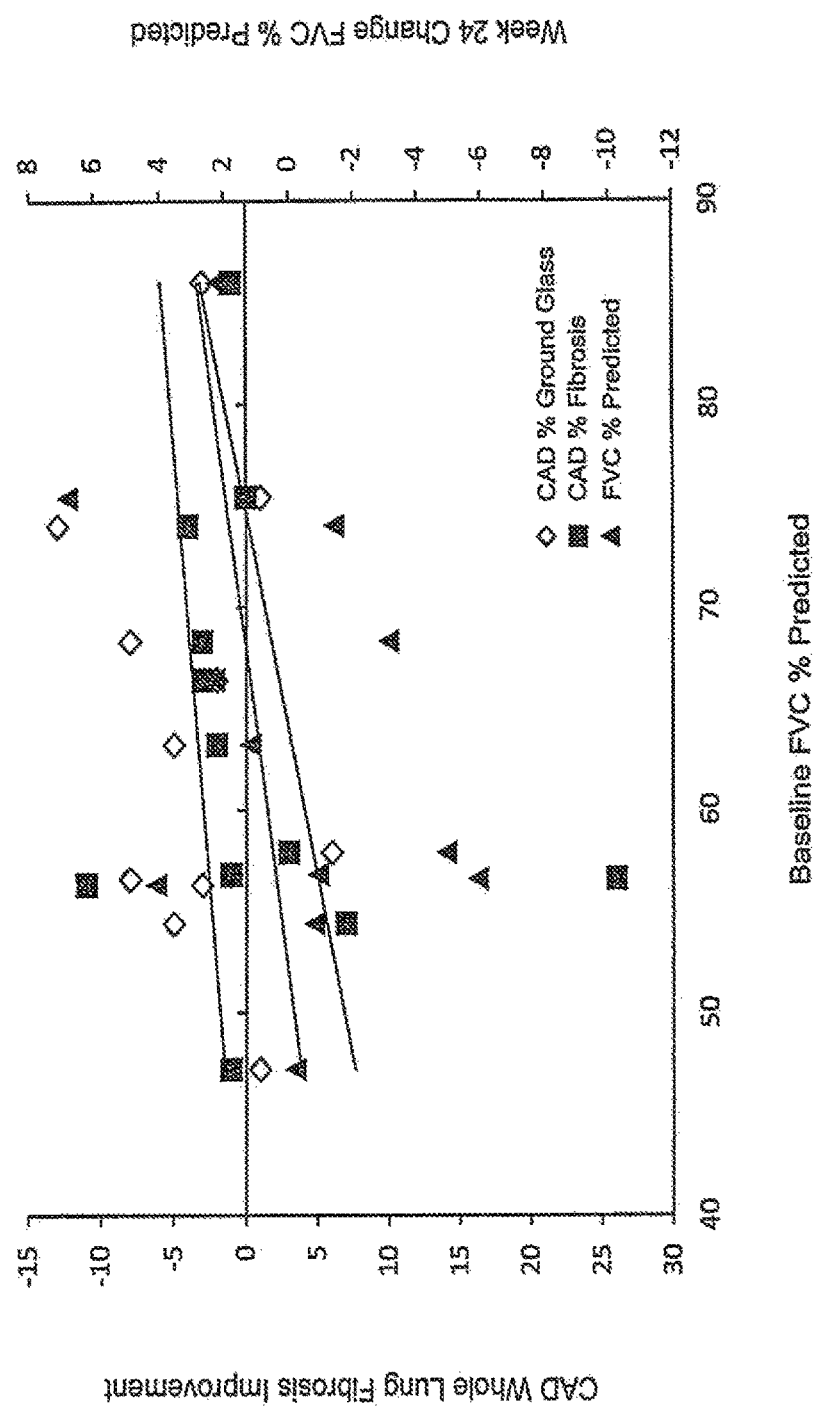
FIG. 6 illustrates the association between improvement in lung structure and improvement in lung function in subjects treated with an anti-CTGF antibody. The improvement in lung structure is shown by the reduction (reversal) of pulmonary radiographic parameters ground glass opacities and fibrosis, i.e., the negative values. The improvement in lung function is shown by the increase in FVC % predicted values (positive change). Generally, subjects with a higher baseline FVC % predicted value, in general, responded better to anti-CTGF antibody therapy.

An examination of the CAD analysis results and Week 24 FVC % predicted values compared to baseline FVC % predicted values demonstrated that the reversals in pulmonary radiographic parameters and the increases in FVC % predicted values were correlated. (FIG. 6) Further, subjects with higher baseline FVC % predicted values, in general, responded better to anti-CTGF antibody therapy. More specifically, a threshold baseline FVC % predicted value, >63%, was found, wherein, subjects who entered the trial with a baseline FVC % predicted >63%, generally showed an improvement in lung fibrosis following treatment with an anti-CTGF antibody, as evidenced by a decrease in the extent of pulmonary radiographic parameters.

Ongoing Data Collection and Analysis

At appropriate time points maximum plasma concentration (Cmax) and trough level (Cmin) of the anti-CTGF antibody (CLN1) are determined. The area under the curve (AUC) for antibody exposure is calculated for subjects using either linear or log-linear extrapolation.

Pulmonary function and DLCO testing is continued through Week 48 and the changes in FVC, FVC % predicted, TLC, FRC, DLCO and DLCO % predicted are analyzed for clinically meaningful responses, such as ≥10% and ≥25% improvements in baseline measurements.

Follow-up HRCT scans at Week 48 are obtained and compared with the baseline HRCT and Week 24 scans by visual scoring and CAD analysis as detailed above for the 24 Week HRCT scans. The proportion of responders and its 95% confidence interval are calculated.

The median progression-free survival is estimated using the Kaplan-Meier method from the analysis of the proportion of subjects who meet the disease progression criteria during the study.

Clinical Trial Update

A total of 54 subjects were enrolled in the study, now termed "Cohort 1," of which 53 subjects were treated. Forty four subjects were seen at Week 24 with 39 subjects completing treatment and follow up. Fifteen subjects withdrew with 5 of the withdrawals voluntary, 3 because of lung transplantation and 6 related to adverse events that were not associated with the anti-CTGF antibody treatment.

Patient demographics of the enrolled subjects include a mean age of 67.3. Eighty three percent of the subjects were male. Disease severity at baseline, measured as FVC % predicted ranged from 42.5% to 86% with a median of FVC % predicted of 63.2% and a mean FVC % predicted of 62.5%. The median DLCO % predicted was 47.0% and the mean DLCO % predicted was 49.5%.

Analysis of plasma samples from subjects for anti-CTGF antibody concentration following the first infusion demonstrated a mean Day 1 Cmax of 336 μg/ml, SD±86 μg/ml, n=35 and a Week 3 mean Cmin of 23 μg/ml, SD±10 μg/ml, n=34. The Week 24 (8$^{th}$ infusion) mean Cmax was 341

μg/ml, SD±115, n=33, similar to the Cmax from the first infusion. The Week 27 Cmin of 42 μg/ml, SD+25 μg/ml, n=30 was higher than the Week 3 Cmin value. The Week 45 mean Cmax was 225 μg/ml, SD=84 μg/ml, n=19. Week 48 mean Cmin was 47 μg/ml, SD=22 μg/ml, n=18.

Figure 7:
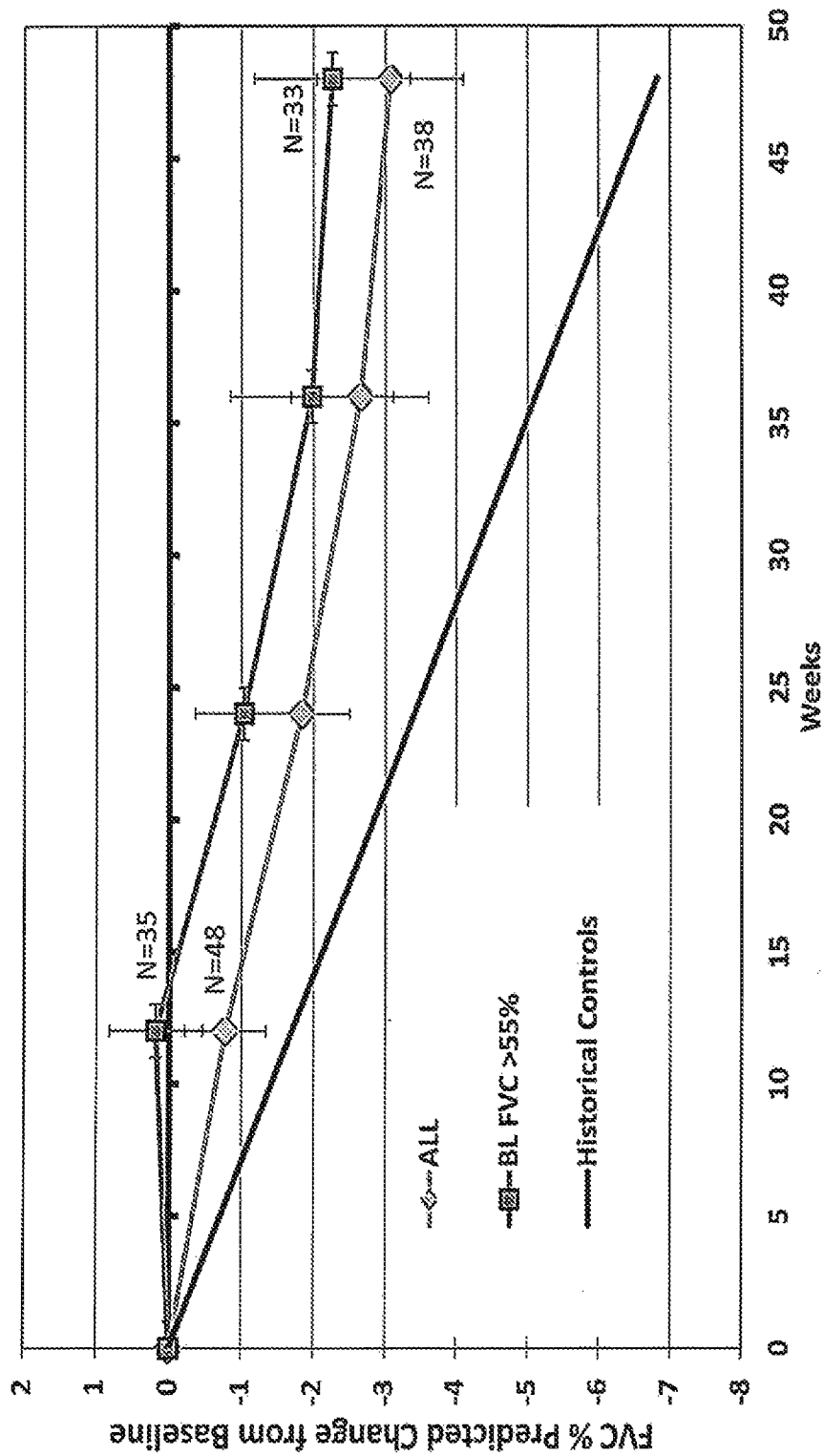
FIG. 7 illustrates that subjects treated with an anti-CTGF antibody (CLN1, ALL) experienced a reduction of the pathologic rate of decline of pulmonary function at all time points, as measured by the change in FVC % predicted from baseline, compared to a composite placebo arm derived from recent IPF clinical trials, n=1,019 The graph further illustrates that subjects with a FVC % predicted baseline value greater than 55% (BL>55%) experienced an even greater reduction in the pathologic rate of decline of pulmonary function compared to all the subjects treated with the anti-CTGF antibody or historical controls.

Testing of pulmonary function parameters demonstrated that the slowing of the pathologic rate of decline in pulmonary function seen with the initial subjects continued. FIG. 7 The rate of decline in FVC % predicted from baseline for all treated subjects was reduced compared to placebo treated historical controls. Additionally, it was noted that subjects enrolled with a baseline FVC % predicted greater than 55% experienced an even greater reduction in the rate of decline of this pulmonary function parameter compared to all subjects treated with an anti-CTGF antibody or historical controls.

Figure 8:
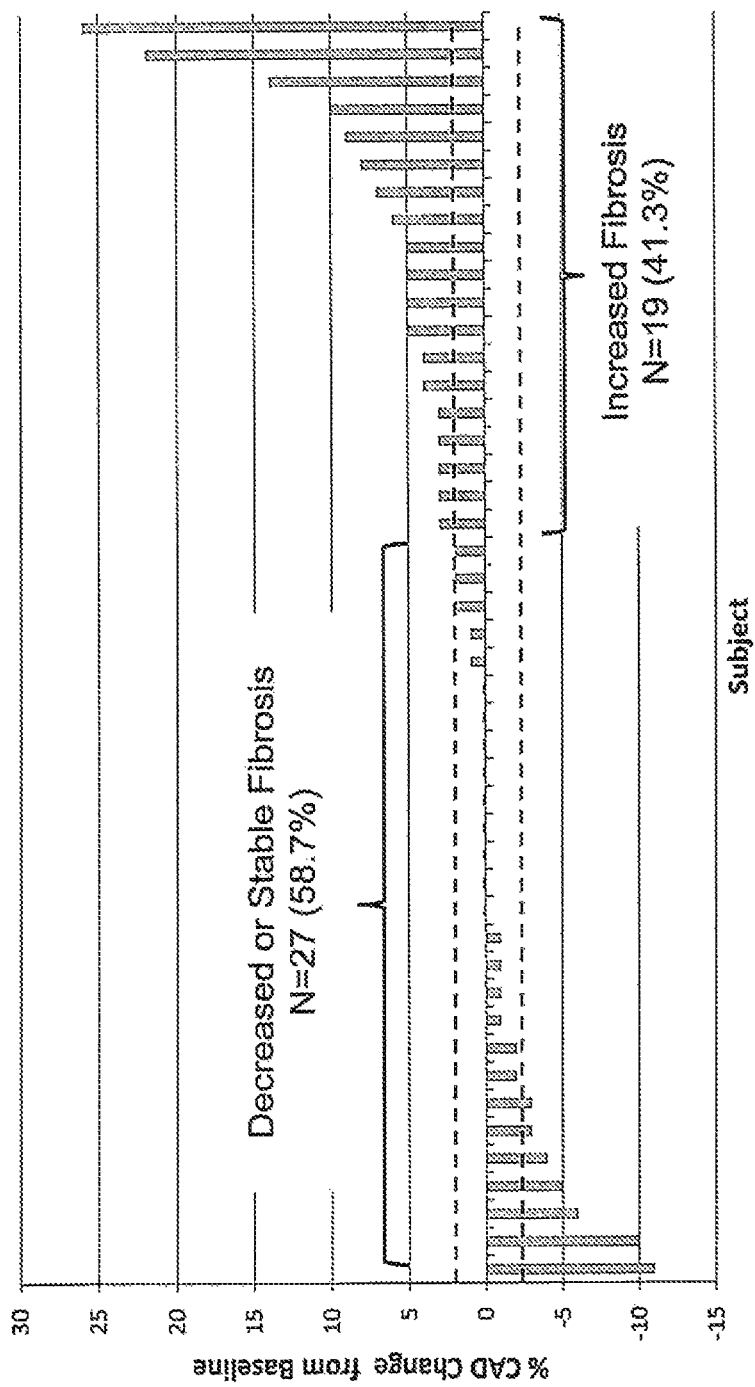
FIG. 8 illustrates, at Week 24, the change from baseline in the pulmonary radiographic parameter fibrosis (F) for whole lung for the completed study using a CAD analysis system, n=46 (includes 2 subjects that withdrew early). The pulmonary radiographic parameter fibrosis decreased (<−2% change) or was stable (±2% change) in 58.7% of the subjects (n=27). An increase (>+2% change) in the pulmonary radiographic parameter fibrosis was seen in 41.3% of the subjects (n=19). The dashed horizontal lines indicate the range of measurement error ±2%.
Figure 9:
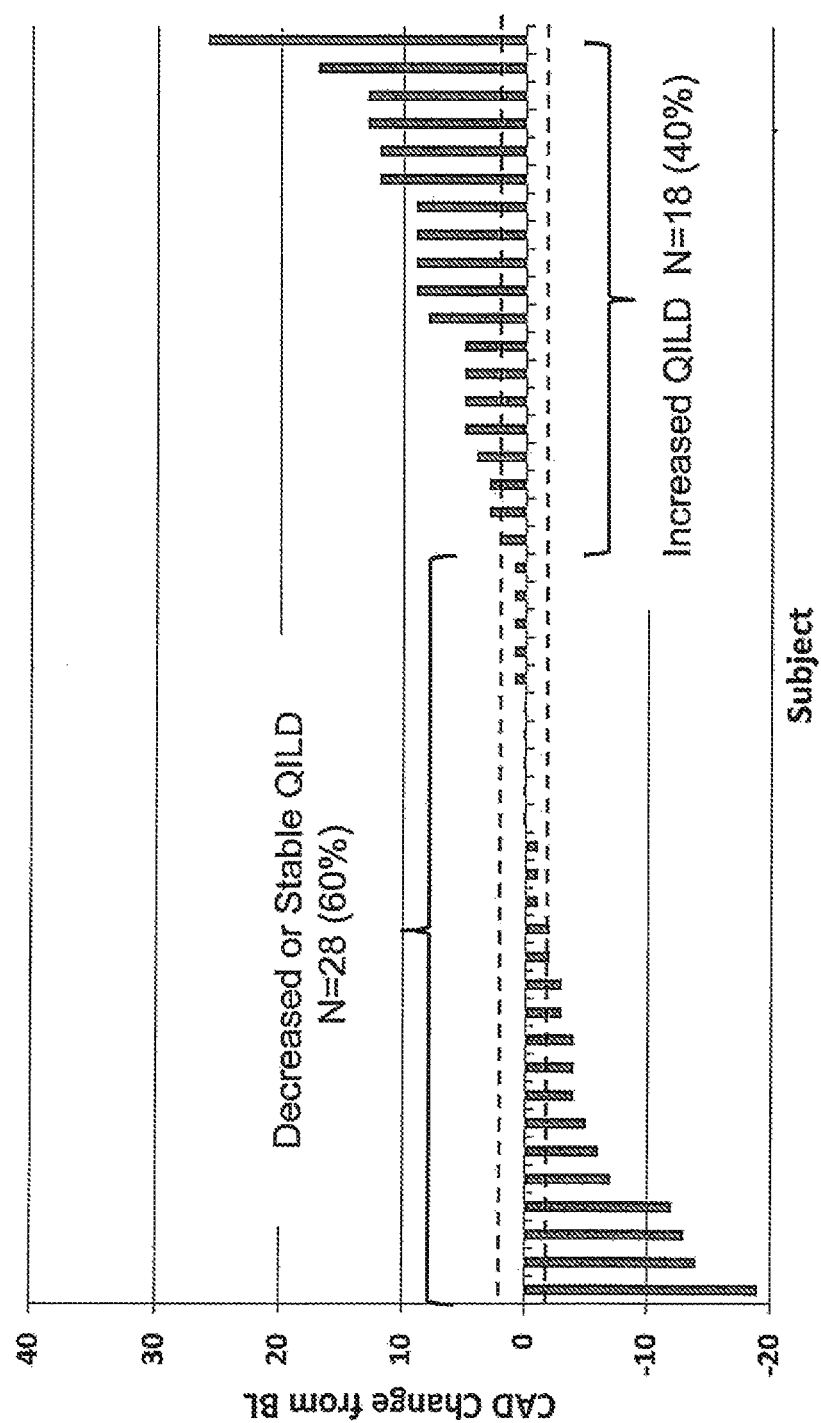
FIG. 9 illustrates, at Week 24, the change from baseline in QILD for whole lung for the completed study using a CAD analysis system, n=46 (includes 2 subjects that withdrew early). Decreased (<−2% change) or stable QILD (±2% change) was noted in 60% of the subjects (n=28). Increased (>+2% change) QILD was seen in 40% of the subjects (n=18). The dashed horizontal lines indicate the range of measurement error ±2%.

The surprising decrease and stabilizations in radiographic pulmonary parameters seen with the initial 12 subjects at Week 24 continued when the HRCT scans of whole lungs from 46 subjects were examined by CAD analysis and compared to their respective baseline HRCT scan. FIGS. 8 and 9. Approximately 59% of the subjects had a decrease (reversal) or stabilization of the radiographic pulmonary parameter, fibrosis. FIG. 8. Similarly, 60% of the subjects had a decrease (reversal) or stabilization of QILD. FIG. 9. CAD analysis of the most severe lung lobe demonstrated similar response rates to whole lung. Additionally, all three radiographic pulmonary parameters proved to be mutable with anti-CTGF antibody therapy. Further, a decrease in QILD was usually associated by a decrease in at least two radiographic pulmonary parameters. Similarly, an increase in QILD was usually associated by an increase in at least two radiographic pulmonary parameters.

Figure 10:
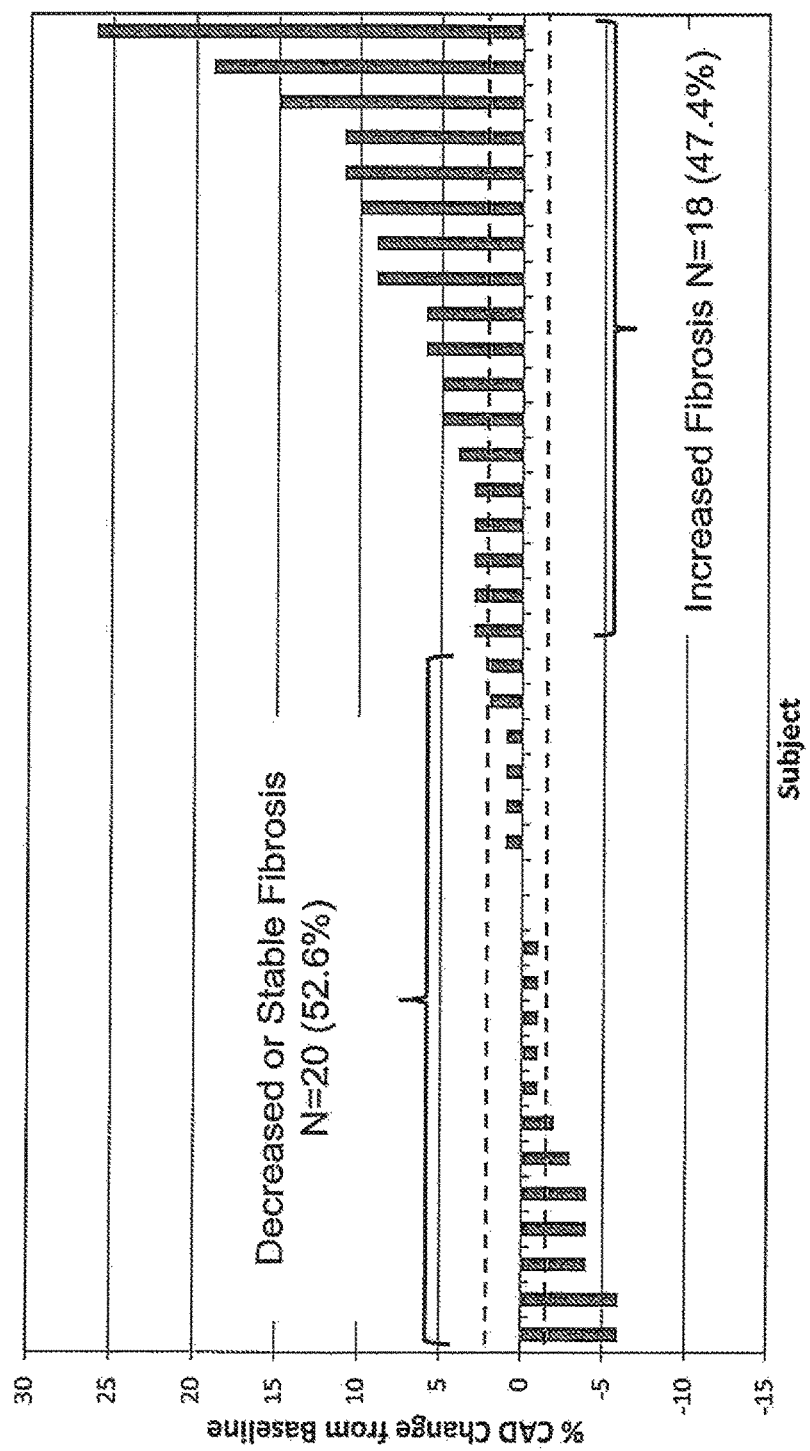
FIG. 10 illustrates, at Week 48, the change from baseline in the pulmonary radiographic parameter fibrosis (F) for whole lung for the completed study using a CAD analysis system, n=38. The pulmonary radiographic parameter fibrosis decreased (<−2% change) or was stable (±2% change) in 52.6% of the subjects (n=20). An increase (>+2% change) in the pulmonary radiographic parameter fibrosis was seen in 47.4% of the subjects (n=18). The dashed horizontal lines indicate the range of measurement error ±2%.
Figure 11:
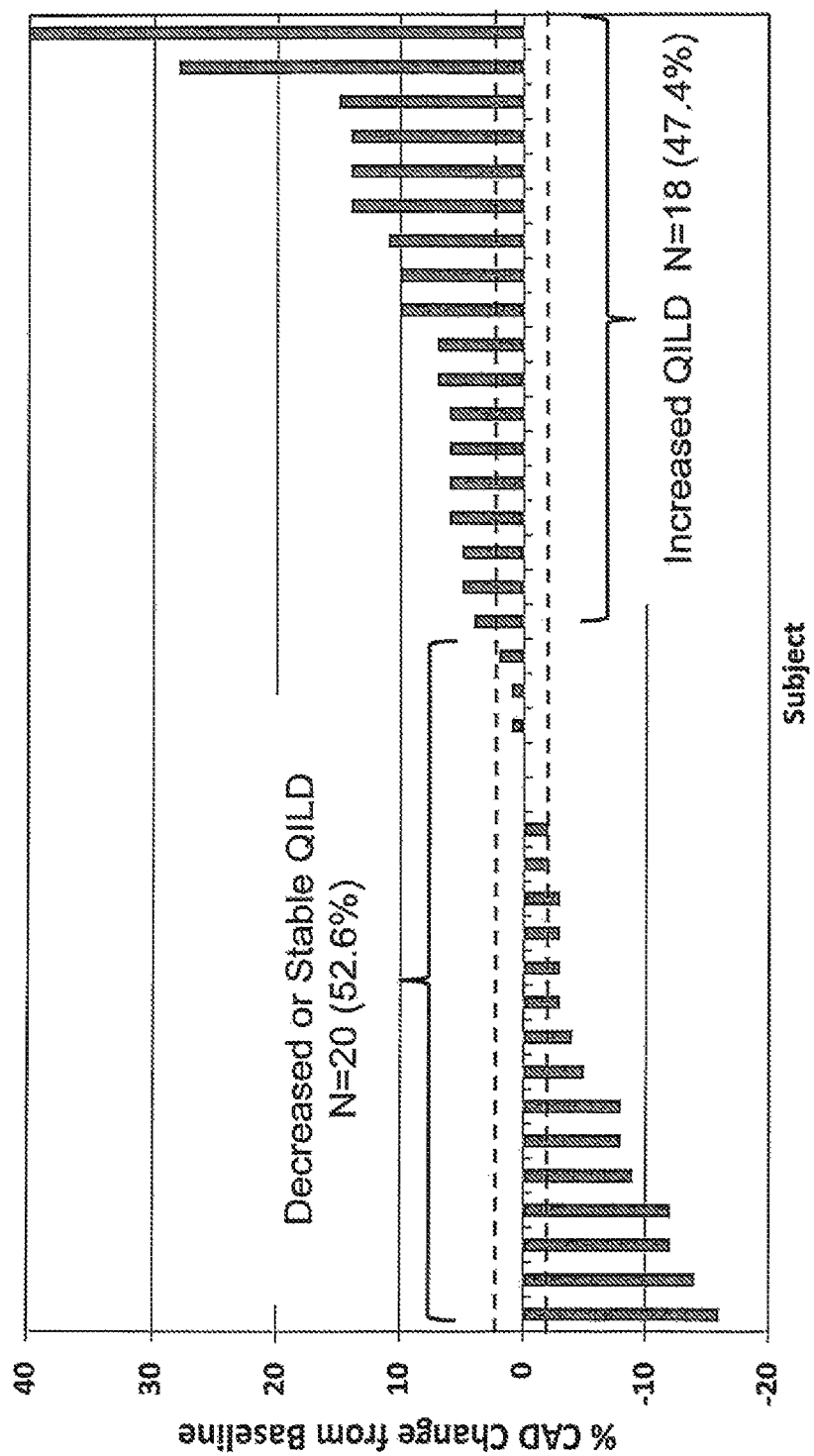
FIG. 11 illustrates, at Week 48, the change from baseline in QILD for whole lung for the completed study using a CAD analysis system, n=38. Decreased (<−2% change) or stable QILD (±2% change) was noted in 52.6% of the subjects (n=20). Increased (>+2% change) QILD was seen in 47.4% of the subjects (n=18). The dashed horizontal lines indicate the range of measurement error ±2%.
Figure 12:
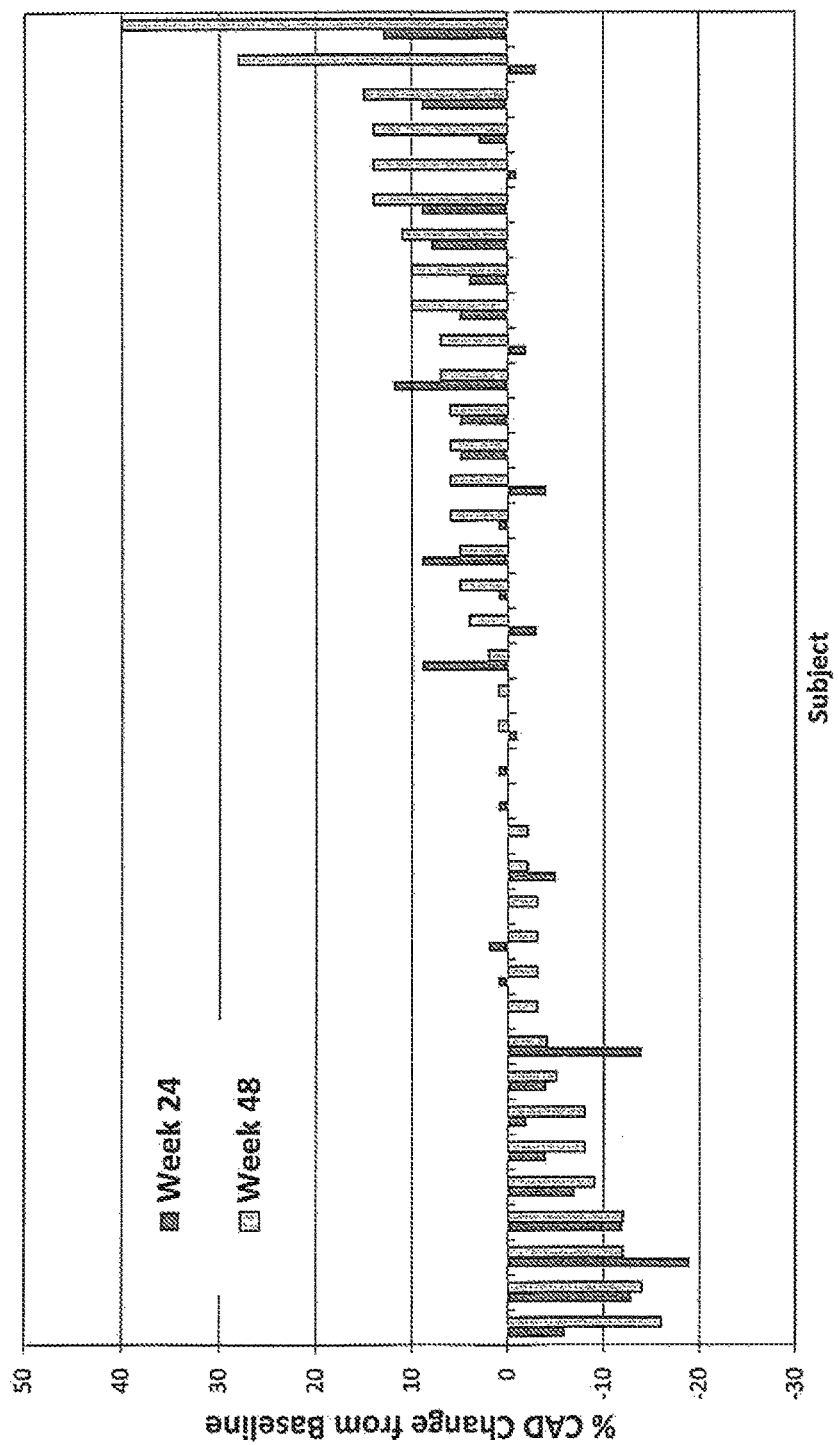
FIG. 12 compares the change from baseline in QILD at Weeks 24 and 48 for individual subjects using a CAD analysis system, n=38. The degree of change in QILD values for individual subjects are fairly consistent for the two time points. Subjects that showed a decrease (<−2%) in QILD at Week 24 usually continued to show a decrease in QILD at Week 48. Subjects that had stable QILD at Week 24 (±2% change) usually continued to show stable QILD at Week 48. Similarly, subjects that showed an increase (>+2%) in QILD at Week 24 usually continued to show an increase in QILD at Week 48.

The decrease (reversal) and stabilization of radiographic pulmonary parameters seen at Week 24 endured to at least Week 48, with slight reductions in the total percentage of subjects within these groups. FIGS. 10 and 11. The response of individual subjects to the anti-CTGF antibody therapy generally persisted over the treatment period. FIG. 12. Subjects that showed a decrease (reversal) in QILD at Week 24 usually continued to show a decrease (reversal) in QILD at Week 48. Subjects that had stable QILD at Week 24 usually continued to show stable QILD at Week 48. Similarly, subjects that showed an increase in QILD at Week 24 usually continued to show an increase in QILD at Week 48. The results demonstrate that CAD analysis of HRCT scans can be used to prognosis subjects with IPF that are treated with an anti-CTGF antibody. In particular, the extent of QILD at Week 24 can be used to select subjects for further treatment with an anti-CTGF antibody. For example, subjects that demonstrate a decrease or stabilization of QILD at Week 24 can be selected to continue treatment with an anti-CTGF antibody, while subjects that demonstrate an increase in QILD can be switched to a different treatment protocol.

Figure 13:
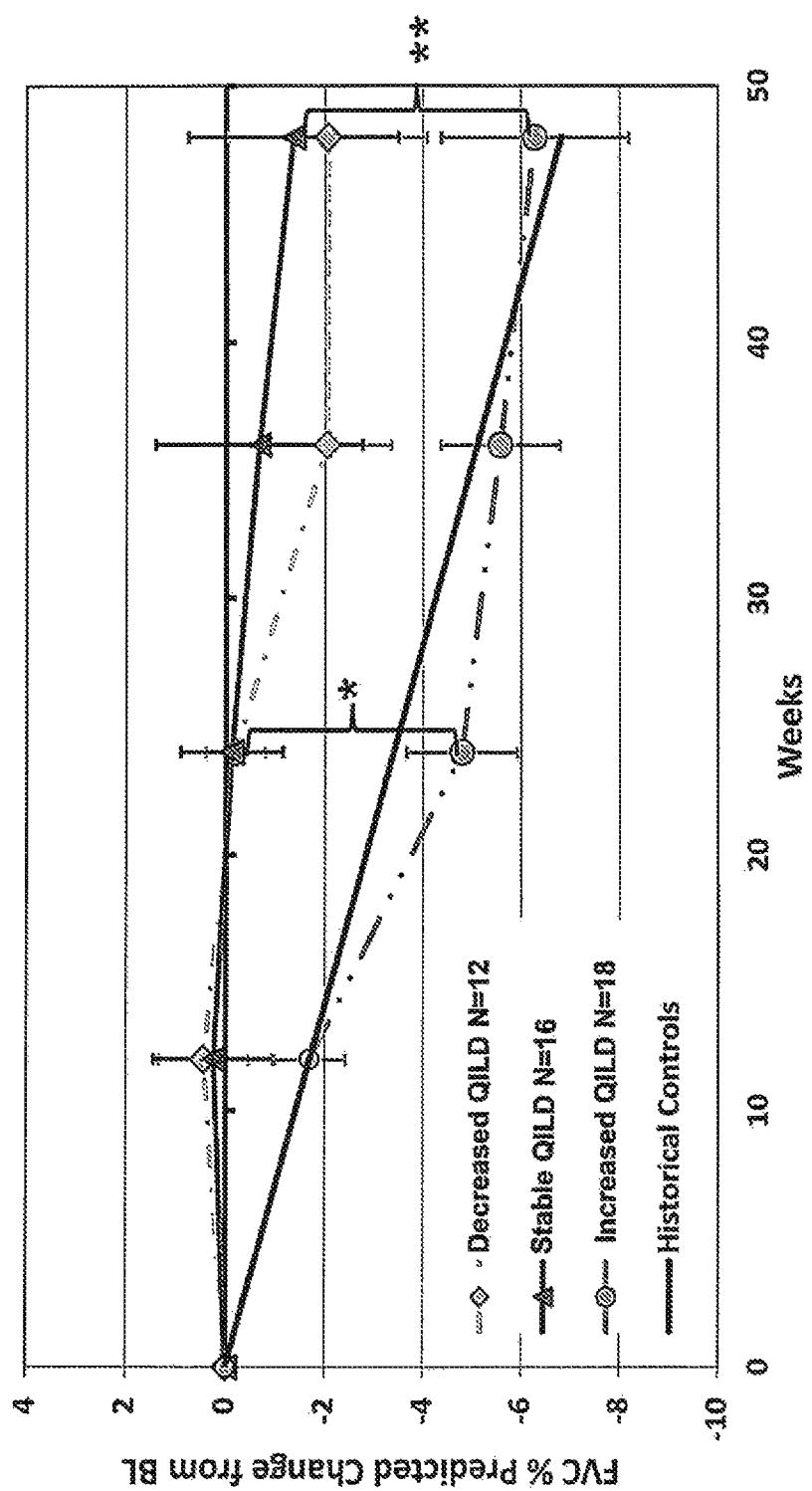
FIG. 13 illustrates the correlation between QILD results at Week 24 for whole lung and the change in FVC % predicted from baseline over the course of the study. Subjects that had an increase (>+2%) in QILD from baseline at Week 24 (Increased QILD) had a pathologic rate of decline in FVC % predicted from baseline that was similar to the pathologic rate of decline in FVC % predicted from baseline seen in historical placebos from recent IPF clinical trials, n=1,019. Subjects that had a decrease (<−2%) in QILD from baseline at Week 24 (Decreased QILD) or stable (±2%) QILD from baseline at Week 24 (Stable QILD) showed similar rates of decline in FVC % predicted from baseline. The difference in the rate of decline in FVC % predicted from baseline between subjects that had increased QILD from baseline at Week 24 and the combined subjects that had stable QILD or decreased QILD from baseline at Week 24, was statistically significant at Week 24 (p<0.004) and Week 48 (p<0.05).

To further explore the relationship between changes in radiographic pulmonary parameters and pulmonary functional parameters, subjects were segregated based on QILD results at Week 24 and their change in FVC % predicted from baseline FVC % predicted compared over time. FIG. 13 Subjects at Week 24 with an increase in QILD compared to baseline QILD continued to lose pulmonary function at a rate similar to historical placebos. In contrast, subjects at Week 24 with a decrease in QILD or stable QILD compared to their baseline QILD had a similar slowing in the pathologic rate of decline of this pulmonary function parameter. The difference in the rate of loss of pulmonary function between those subjects that showed an increase in QILD from baseline at 24 weeks and the subjects from the combined group of subjects that at 24 weeks had a decrease in QILD or stable QILD compared to baseline was statistically significant (p<0.004). The difference in pulmonary function between these groups continued through at least Week 48 (p<0.05). These results demonstrate correlation between stabilization or improvement in lung morphology via HRCT and improvement in pulmonary function. These results further confirm that changes in lung morphology determined by serial radiographic measurements can be used to prognosis subjects that receive anti-CTGF antibody therapy for IPF. In particular, these results demonstrate that changes in the extent of QILD at Week 24 can be used to prognosis subjects. Subjects with stable or decreased QILD at Week 24 compared to baseline generally have a marked reduction in the pathologic rate of decline of FVC % predicted. This reduction in the rate of decline is maintained at least through Week 48 with continued treatment with an anti-CTGF antibody. On the other hand, subjects that have increased QILD at Week 24 compared to baseline generally continue to show a rate of decline in FVC % predicted that is similar to historical controls. Subjects at Week 24 that have increased QILD compared to their QILD at baseline can be switched to a different treatment protocol that may include a higher anti-CTGF antibody dose.

Figure 14:
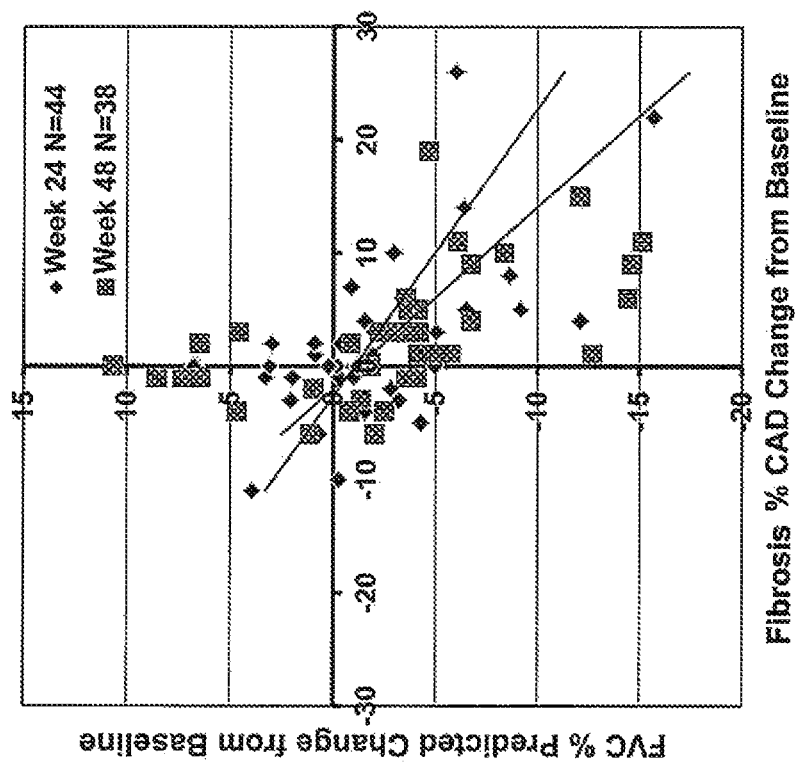
FIG. 14 illustrates that the change in FVC % predicted from baseline is associated with the change from baseline in the pulmonary radiographic parameter fibrosis, as determined using a CAD analysis system.
Figure 15:
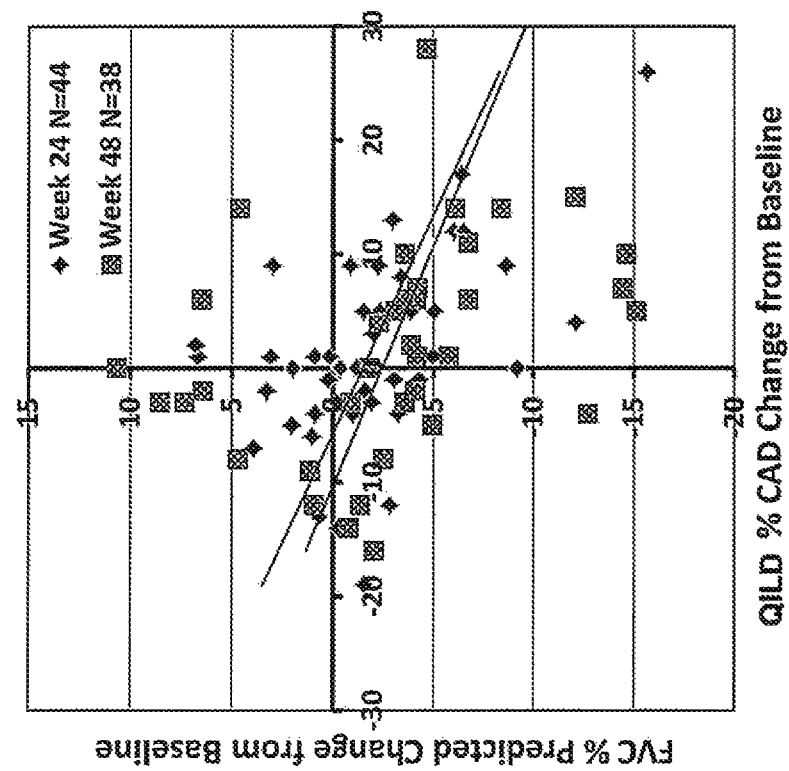
FIG. 15 illustrates that the change in FVC % predicted from baseline is associated with the change from baseline in QILD, as determined using a CAD analysis system.

The relationship between the improvements in radiographic pulmonary parameters and improvements in pulmonary function parameters for subjects treated with an anti-CTGF antibody were further examined by correlation analyses. FIGS. 14 and 15 and Table 6 The analyses show that the reduction in pulmonary fibrosis from baseline, as measured radiographically, correlates with the improvement in pulmonary function, as measured by the change in FVC % predicted from baseline, in subjects that received anti-CTGF antibody therapy.

TABLE 6

| Pearson Correlation Analysis | | | | |
|---|---|---|---|---|
| | Δ FVC % Predicted vs Δ Fibrosis (Shown in FIG. 14) | | Δ FVC % Predicted vs Δ QILD (Shown in FIG. 15) | |
| | Week 24 | Week 48 | Week 24 | Week 48 |
| N | 44 | 38 | 44 | 38 |
| $r_s$ | −0.6004 | −0.5575 | −0.4934 | −0.3514 |
| p value | 0.000016 | 0.000277 | 0.000667 | 0.030502 |

Figure 16:
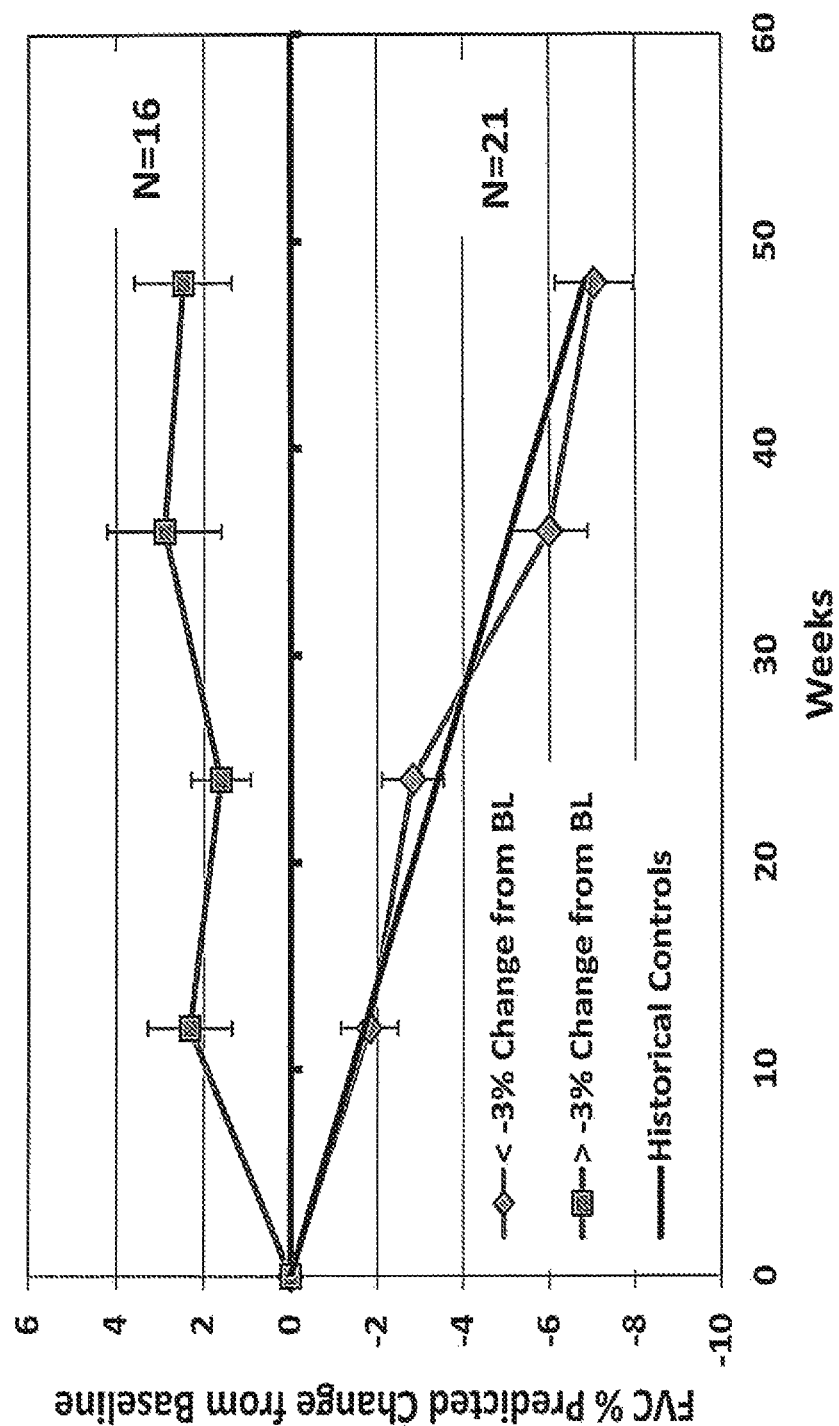
FIG. 16 illustrates the rate of decline in FVC % predicted values from baseline over time for subjects above and below a threshold −3% change in FVC % predicted at Week 48. Subjects above the threshold value (>−3%) at Week 48 (40% of total subjects) had at Week 12, a slight increase in pulmonary function that was maintained for at least 48 weeks. In contrast, subjects below the threshold value (<−3%) at Week 48 (60% of total subjects) showed a continual decline in pulmonary function that was similar to the results seen in historical placebos from recent IPF clinical trials, n=1019.

The change in FVC % predicted outcomes at Week 48 was examined for subjects that experienced less than a −3% change from baseline and subjects that experienced greater than a −3% change from baseline at Week 48. FIG. 16 The results show that at Week 48, subjects that experienced a change in FVC % predicted above −3% compared to baseline (40% of total subjects) initial gained a slight increase in pulmonary function at Week 12 that was maintained to at least Week 48. In contrast, at Week 48 subjects that experienced change in FVC % predicted below −3% compared to baseline (60% of total subjects) showed a continual decline in pulmonary function that was similar to the results seen in historical placebo controls. The results demonstrate that in general, subjects that experience at most a modest decline (<−3% change) in FVC % predicted gained pulmonary function following treatment with an anti-CTGF antibody.

Subjects that experienced less than a −3% change in FVC % predicted from baseline at Week 48 were allowed to continue treatment for a second year (15 mg/kg IV Q 3 weeks for a total of 45 weeks) to test the hypothesis that longer treatment with an anti-CTGF antibody would maintain or even improve pulmonary function parameters. Nineteen subjects elected to continue treatment and will be monitored as before with testing of pulmonary function parameters every 12 weeks and HRCT scans at Weeks 24 and 48 of this second treatment course.

In summary, the clinical data from Cohort 1 demonstrate that treatment with an anti-CTGF antibody can slow the pathologic rate of decline in pulmonary function in subjects with IPF. Further, in some subjects, treatment with an anti-CTGF antibody can improve pulmonary function or stop the decline (stabilize) in pulmonary function. Additionally, treatment with an anti-CTGF antibody can reverse pulmonary fibrosis or prevent the progression (stabilize) of pulmonary fibrosis as evidenced by changes in radiographic images over time. Notably, the improvements seen in pulmonary function are associated with the improvements in pulmonary structure, i.e., reversal or stabilization of radiographic pulmonary parameters. The results support the continued treatment of subjects with the anti-CTGF antibody CLN1 at 15 mg/kg and the initiation of a second therapy arm to study the therapeutic response to a higher antibody dose.

Cohort 2

Based on the surprising results achieved with the administration of 15 mg/kg of an anti-CTGF antibody, coupled with knowledge that the use of the anti-CTGF antibody, CLN1, in other indications at a dose of up to 45 mg/kg IV Q 2 weeks has not identified any significant safety concerns, a second cohort for treatment of IPF was initiated. Subjects are being treated with 30 mg/kg IV Q 3 weeks. The entry criteria for Cohort 2 is the same as Cohort 1 with the exception that eligible subjects require a FVC % predicted ≥55%. To date, 32 subjects are enrolled.

Figure 17:
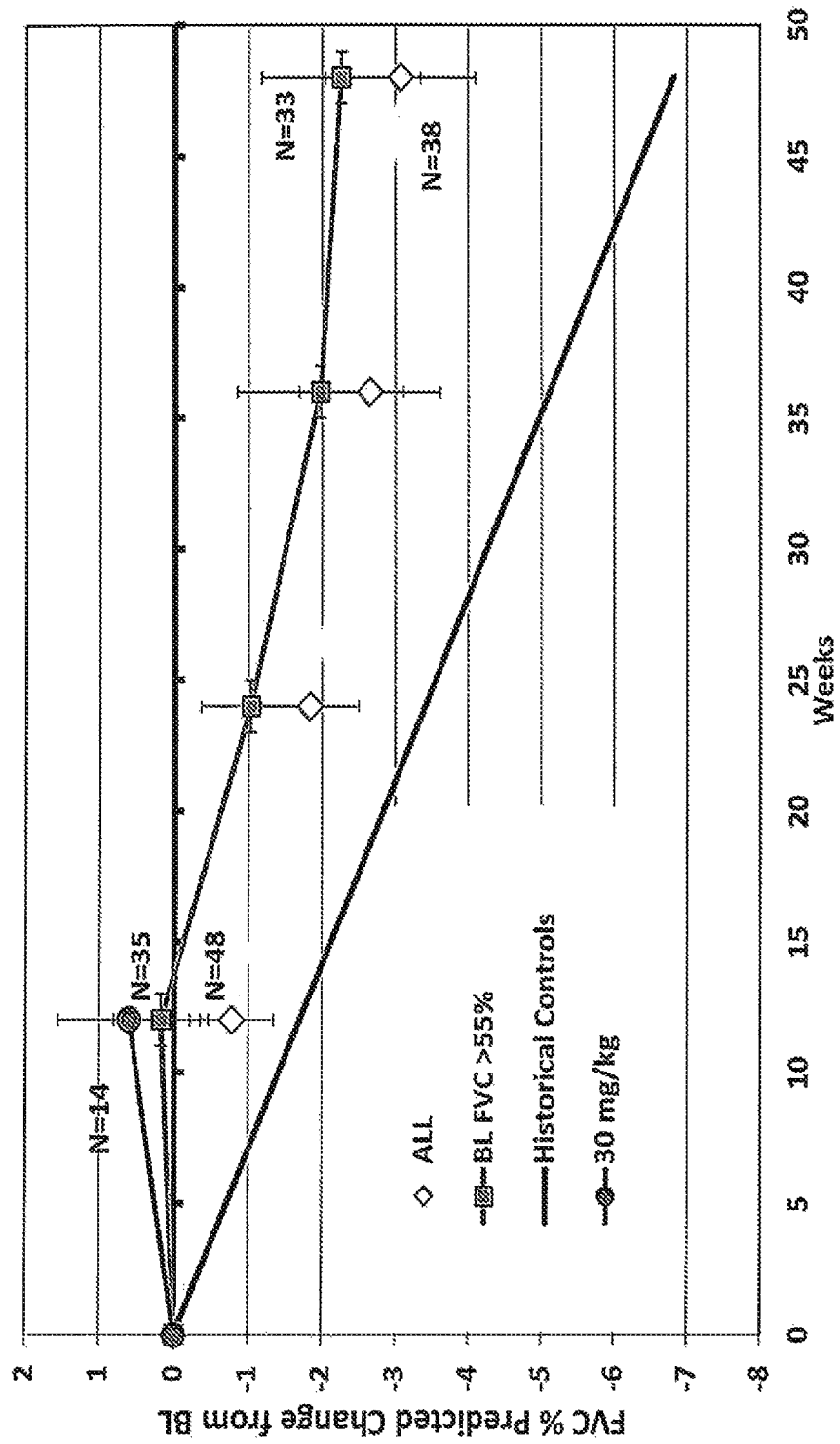
FIG. 17 illustrates the positive change (reversal) in FVC % predicted from baseline at Week 12 for the first 14 subjects enrolled in Cohort 2, compared to the results of Cohort 1 and historical controls. Subjects in Cohort 2 received 30 mg/kg of an anti-CTGF antibody. The initial measurement shows that the change in FVC % predicted from baseline for the 30 mg/kg group is higher than that seen in the subjects that received 15 mg/kg, including those subjects in Cohort 1 that had a baseline FVC % predicted of greater than 55%.

Initial pulmonary function study results at Week 12 for 14 subjects suggest that a higher antibody dose can further improve pulmonary function parameters. FIG. 17 Subjects experienced a reversal in the expected rate of decline from baseline of FVC % predicted values, i.e., the change in their FVC % predicted values rose was positive demonstrating an improvement in pulmonary function compared to baseline.

Safety Profile

Treatment with the anti-CTGF antibody, CLN1, is well tolerated. The pattern of adverse events was consistent with the demographics and underlying disease in the population being studied. At Week 36, no serious adverse events were assessed as related to treatment with CLN1 and there were 3 deaths, all related to progression of IPF, and one acute exacerbation of IPF to date in enrolled subjects.

Through the completion of Cohort 1, no significant safety concerns related to the administration of CLN1 were identified. Additionally, there were no further deaths or acute exacerbations of IPF.

What is claimed:

1. A method for treating idiopathic pulmonary fibrosis (IPF) in a subject in need thereof, the method comprising:
    (a) taking a baseline measurement of a pulmonary radiographic parameter, wherein the pulmonary radiographic parameter is fibrosis;
    (b) administering at least 15 mg/kg of an anti-CTGF antibody every three weeks, thereby stabilizing or producing at least a 2% reduction in fibrosis compared to the baseline measurement, wherein the anti-CTGF antibody is identical to the antibody produced by the cell line identified by ATCC Accession No. PTA-6006.

2. The method of claim 1 wherein administration of the anti-CTGF antibody also stabilizes or produces at least a 2% redaction, compared to a baseline measurement, in a pulmonary radiographic parameter selected from the group consisting of ground glass opacity and honeycomb formation.

3. The method of claim 1, wherein the subject has a forced vital capacity percent (FVC %) predicted of greater than about 55% prior to treatment with the anti-CTGF antibody.

4. The method of claim 1, wherein the subject has less than 50% parenchymal fibrosis prior to treatment with the anti-CTGF antibody.

5. The method of claim 1, wherein the subject has less than 25% honeycombing within the whole lung prior to treatment the anti-CTGF antibody.

* * * * *